US008663935B2

(12) United States Patent
Wolfers et al.

(10) Patent No.: US 8,663,935 B2
(45) Date of Patent: Mar. 4, 2014

(54) MULTICOLOR FLOW CYTOMETRY COMPOSITIONS CONTAINING UNCONJUGATED PHYCOBILIPROTEINS

(75) Inventors: Joseph Wolfers, La Bouilladisse (FR); Fabrice Malergue, Marseille (FR); Ravinder K. Gupta, Pembroke Pines, FL (US); Lori A. Charie, Pembroke Pines, FL (US); Francisco Estevez-Labori, Miami Beach, FL (US); Meryl Forman, Miami, FL (US); Emmanuel Gautherot, Marseille (FR)

(73) Assignee: Beckman Coulter, Inc., Brea, CA (US)

( * ) Notice: Subject to any disclaimer, the term of this patent is extended or adjusted under 35 U.S.C. 154(b) by 393 days.

(21) Appl. No.: 12/635,063

(22) Filed: Dec. 10, 2009

(65) Prior Publication Data

US 2010/0151493 A1   Jun. 17, 2010

Related U.S. Application Data

(60) Provisional application No. 61/121,923, filed on Dec. 12, 2008.

(51) Int. Cl.
*G01N 33/533* (2006.01)

(52) U.S. Cl.
USPC .......................................... 435/7.2; 435/7.21

(58) Field of Classification Search
None
See application file for complete search history.

(56) References Cited

U.S. PATENT DOCUMENTS

| 4,542,104 | A | * | 9/1985 | Stryer et al. | 436/536 |
|---|---|---|---|---|---|
| 4,857,474 | A | * | 8/1989 | Waterbury et al. | 436/501 |
| 5,272,257 | A | * | 12/1993 | Gupta | 530/370 |
| 5,695,990 | A | * | 12/1997 | Cubicciotti | 435/317.1 |
| 5,714,386 | A | | 2/1998 | Roederer | |
| 5,994,089 | A | * | 11/1999 | Siiman et al. | 435/7.24 |
| 6,146,837 | A | * | 11/2000 | van de Winkel | 435/7.1 |
| 6,342,389 | B1 | * | 1/2002 | Cubicciotti | 435/317.1 |
| 6,703,216 | B2 | | 3/2004 | Parson | |
| 6,809,186 | B1 | * | 10/2004 | Morseman et al. | 530/409 |
| 7,128,875 | B2 | * | 10/2006 | Cubicciotti | 422/82.05 |
| 7,256,050 | B2 | * | 8/2007 | Morseman et al. | 436/172 |

(Continued)

FOREIGN PATENT DOCUMENTS

| WO | 98/52040 | | 11/1998 | | |
|---|---|---|---|---|---|
| WO | 01/96383 | * | 12/2001 | ........... | C07K 14/195 |
| WO | 01/96871 | * | 12/2001 | ............. | G01N 33/53 |
| WO | 03/005972 | | 1/2003 | | |

OTHER PUBLICATIONS

Johnson, TR et al, Journal of Bacteriology, vol. 170(4), pp. 1858-1865, 1998, Structure and regulations of genes encoding phycocyanin and allophycocyanin from *Anabaena variabilis* ATCC 29413.*

(Continued)

*Primary Examiner* — Albert Navarro
*Assistant Examiner* — Ginny Portner
(74) *Attorney, Agent, or Firm* — K&L Gates LLP; Louis C. Cullman; Georgia Kefallinos

(57) ABSTRACT

Novel compositions containing (i) ligand conjugated phycobiliprotein tandem dyes and (ii) unconjugated phycobiliproteins are provided wherein the phycobiliproteins are derived from the same bacterial or eukaryotic algae species. The phycobiliproteins must be the same or different, but must contain some non-crosslinked subunits which exchange. Also provided are methods for preparing these compositions, kits containing these compositions or components of the same, and methods of using these compositions for cellular and non-cellular analysis.

19 Claims, 14 Drawing Sheets

(56) References Cited

U.S. PATENT DOCUMENTS

| | | | | |
|---|---|---|---|---|
| 7,531,179 | B2* | 5/2009 | Atassi | 424/197.11 |
| 7,662,920 | B2* | 2/2010 | Geiger et al. | 530/350 |
| 8,008,545 | B2* | 8/2011 | Plesch et al. | 800/288 |
| 2001/0055783 | A1* | 12/2001 | Allnutt et al. | 435/7.92 |
| 2002/0061601 | A1* | 5/2002 | Morseman et al. | 436/524 |
| 2003/0134325 | A1* | 7/2003 | Cubicciotti | 435/7.1 |
| 2005/0069958 | A1 | 3/2005 | Mills | |
| 2006/0024744 | A1* | 2/2006 | Mills et al. | 435/7.1 |
| 2006/0121503 | A1 | 6/2006 | Diwu | |
| 2006/0137042 | A1* | 6/2006 | Plesch et al. | 800/288 |
| 2006/0160998 | A1* | 7/2006 | Suk | 530/391.1 |
| 2007/0009931 | A1* | 1/2007 | Kirsch | 435/6 |
| 2007/0015215 | A1* | 1/2007 | Cubicciotti | 435/7.1 |
| 2007/0265430 | A1* | 11/2007 | Geiger et al. | 530/350 |
| 2008/0020393 | A1* | 1/2008 | Kirsch et al. | 435/6 |
| 2008/0131914 | A1 | 6/2008 | Ahearn | |

OTHER PUBLICATIONS

Brejc, K et al, Journal of Molecular Biology, 1995, vol. 249, pp. 424-440, Isolation, Crystallization, Crystal Structure Analysis and Refinement of Allophycocyanin from the Cyanobacterium *Spirulina platensis* at 2.3A Resolution.*

Bryant, Donald A et al, Archive in Microbiology, 1981, vol. 129, pp. 190-198, Characterization of the Biliproteins of *Gloeobacter violaceus* Chromophore Content of a Cyanobacterial Phycoerythrin Carrying Phycourobilin Chromophore.*

Rippka, R et al, Journal of General Microbiology, 1979, vol. 111, pp. 1-61, Generic Assignments, Strain Histories and Properties of Pure Clutures of Cyanobacteria.*

Ohki, Kaori et al, Plant Physiology, 1985, vol. 79, pp. 943-948, Constant Phycobilisome size in chromatically adapted cells of the Cyanobacterium Tolypothrix tenuis and Variation in *Nostoc* sp.*

Roederer et al, Cytometry, vol. 24, pp. 191-197, 1996, Cy7PE and Cy7APC:Bright New Probes for Immunofluorescence.*

Telford, William G et al, Journal of Immunological Methods, vol. 254, pp. 13-30, 2001, Cyanobacterial stabilized phycobilisomes as fluorochromes for extracellular detection by flow cytometry.*

Soundarapandian, S et al, Journal of Applied Phycol. 2008, vol. 20, pp. 113-136, Phycobiliproteins as a commodity: trends in applied research, patents and commercialization.*

Liu, J et al, Journal of Biological Chemistry, vol. 274(24), Jun. 11, 1999, pp. 16945-16952, Crystal structure of Allophycocyanin from Red Algae *Porphyra yezoensis* at 2.2 A Resolution.*

Telford, William G et al, Journal of Immunological Methods, vol. 254, (2001), pp. 13-30, Cyanobacterial stablized phycobilisomes as fluorochromes for extracellular antigen detection by flow cytometry.*

Rumbeli, Robert et al, Biol. Chem. Hoppe-Seyler, vol. 368, pp. 1179-1191, Sep. 1987, Crosslinking of Phycobiliproteins from the Cyanobacterium Mastigocladus laminosus with Bis-Imidates: localization of an Intrasubunit and Intersubunit crosslink in C-phycocyanin.*

Wei, A et al, Analytic Chemistry, vol. 66, pp. 1500-1566, 1994, Antibody medicated fluorescence Enhancement Based on shifting the intermolecular dimer-monomer equilibrium of fluorescent dyes.*

Zhu, H et al, Analytical Chemistry, vol. 66(13), Jul. 1, pp. 1941-1948, 1994, High Sensitivity Capillary Electrophoresis of Double stranded DNA fragments using monomeric and dimeric fluorescent intercalating dyes.*

Extended European Search Report dated Jun. 29, 2012 for EP patent application 09832526.9.

Waggoner, A New Fluorescent Antibody Label for Three-Color Flow Cytometry with a Single Laser, New York Academy of Sciences, Annals, Wiley Blackwell Publishing, Inc. US vol. 677, Mar. 20, 1983, pp. 185-193.

Lundell, "Allophycocyanin B. A common β subunit in *Synechococcus allophycocyanin* B ($\lambda_{max}$ 670 nM) and allophycocyanin ($\lambda_{max}$ 650 nM)", Journal of Biological Chemistry, 256(23):12600 (Dec. 10, 1981).

Trinquet, "Allophycocyanin 1 as a near-infrared fluorescent tracer: Isolation, characterization, chemical modification, and use in a homogeneous fluorescence resonance energy transfer system", Analytical Biochemistry, 296:232 (Sep. 15, 2001; e-publication: Aug. 15, 2001).

MacColl, "The relationship of the quaternary structure of allophycocyanin to its spectrum", Archives of Biochemistry and Biophysics, 208(1):42 (Apr. 15, 1981).

MacColl, "Stability of allophycocyanin's quaternary structure", Archives of Biochemistry and Biophysics, 228(1):24 (May 1983).

Ong, "Crosslinking of allophycocyanin", Physiology Végétale, 23:777 (1985).

Yeh, "Fluorescence properties of allophycocyanin and a crosslinked allophycocyanin trimer", Cytometry, 8:91 (Jan. 1987).

Isailovic, "Isolation and characterization of R-phycoerythrin subunits and enzymatic digests" Journal of Chromatography A, 1051:119 (Oct. 8, 2004; e-publication: Aug. 20, 2004).

Combined International Search Report and Written Opinion issued in International Patent Application No. PCT/US09/67481, Feb. 5, 2010, 7 pages.

* cited by examiner

MULTICOLOR FLOW CYTOMETRY COMPOSITIONS CONTAINING UNCONJUGATED PHYCOBILIPROTEINS

CROSS-REFERENCE TO RELATED APPLICATIONS

This application claims the benefit of the priority of U.S. Provisional Patent Application No. 61/121,923, filed Dec. 12, 2008. This priority application is incorporated by reference herein.

BACKGROUND OF THE INVENTION

Phycobiliproteins and their tandem dyes are important fluorochromes that are widely used as fluorescent labels in flow cytometry. The use of tandem dyes has expanded the capability for expanded multi-color analysis in flow cytometry by providing additional fluorochromes with distinct emission spectra using a single donor dye excited by one laser line.

When using many tandem dyes in multicolor combinations, difficulties in discriminating among fluorescence signals can occur. To date, the art has generally ascribed these "difficulties" as being due to dye instability. However, there have not been any definitive answers or suggestions for addressing these problems. Therefore, there remains a need in the art for compositions and methods for analysis which use unique combinations of phycobiliprotein-conjugated ligands. In particular, there remains a need in the art for phycobiliprotein containing tandem dye compositions that limit degradation over time encountered with compositions known in the art.

SUMMARY OF THE INVENTION

For ease of understanding, the terms "first", "second", "third", etc., as applied to a phycobiliprotein, ligand, dye or species in the following summary and detailed description are used to distinguish one phycobiliprotein, ligand, dye or species from another phycobiliprotein, ligand, dye or species, respectively, when present in the same composition. These terms are not employed to identify quantity, order or degree of importance.

In one aspect, a composition is provided that contains a first ligand conjugated to a first tandem dye. The first tandem dye includes a first phycobiliprotein that includes crosslinked and non-crosslinked subunits and a first partner dye conjugated to the first phycobiliprotein. The composition also contains an unconjugated second phycobiliprotein. The first phycobiliprotein and the second phycobiliprotein are derived from a first (i.e., same) bacterial species or eukaryotic algae species. In one embodiment, the first phycobiliprotein and the second phycobiliprotein are the same. In another embodiment, the first and second phycobiliproteins are different and the second phycobiliprotein contains non-crosslinked subunits that exchange with the non-crosslinked subunits of the first phycobiliprotein.

In another aspect, the composition as described above further contains a second ligand conjugated to a second tandem dye. The second tandem dye includes a third phycobiliprotein and a second partner dye conjugated to the third phycobiliprotein. The third phycobiliprotein contains crosslinked and non-crosslinked subunits and is derived from the first bacterial or eukaryotic algae species. This composition also contains an unconjugated fourth phycobiliprotein that includes subunits. The fourth phycobiliprotein also is derived from the first bacterial or eukaryotic algae species. In one embodiment, the first, second, third, and fourth phycobiliproteins are the same. In another embodiment, the fourth phycobiliprotein is different from the first, second, and third phycobiliproteins and the fourth phycobiliprotein contains non-crosslinked subunits that exchange with the non-crosslinked subunits of the first, second, and third phycobiliproteins.

In a further aspect, the composition as described above contains a third ligand conjugated to a third tandem dye. The third tandem dye contains a fifth phycobiliprotein and a third partner dye conjugated to the fifth phycobiliprotein. The fifth phycobiliprotein contains crosslinked and non-crosslinked subunits and is derived from the first bacterial or eukaryotic algae species. This composition also contains an unconjugated sixth phycobiliprotein. The unconjugated sixth phycobiliprotein contains subunits and is derived from the first bacterial or eukaryotic algae species. In one embodiment, the first, second, third, fourth, fifth, and sixth phycobiliproteins are the same. In another embodiment, the sixth phycobiliprotein is different from the first, second, third, fourth, and fifth phycobiliproteins and the sixth phycobiliprotein contains non-crosslinked subunits that exchange with the non-crosslinked subunits of the first, second, third, fourth, and fifth phycobiliproteins.

In still another embodiment, the composition as described above also contains a fourth ligand conjugated to a fourth tandem dye. The fourth tandem dye includes a seventh phycobiliprotein and a fourth partner dye conjugated to the seventh phycobiliprotein. The seventh phycobiliprotein contains crosslinked and non-crosslinked subunits and is derived from the first bacterial or eukaryotic algae species. The composition also contains an unconjugated eighth phycobiliprotein. The unconjugated eighth phycobiliprotein contains subunits and is derived from the first bacterial or eukaryotic algae species. In one embodiment, the first, second, third, fourth, fifth, sixth, seventh, and eighth phycobiliproteins are the same. In another embodiment, the eighth phycobiliprotein are different from the first, second, third, fourth, fifth, sixth, and seventh phycobiliproteins and the eighth phycobiliprotein contains non-crosslinked subunits that exchange with the non-crosslinked subunits of the first, second, third, fourth, fifth, sixth, and seventh phycobiliproteins.

In another aspect, any of the above-described compositions includes one or more additional ligands conjugated to a dye that is not a phycobiliprotein.

In still another aspect, the above-described composition containing the first ligand conjugated to the first tandem dye and the unconjugated second phycobiliprotein also includes one or more additional ligands conjugated to a third phycobiliprotein which is derived from the first bacterial or eukaryotic algae species. In one embodiment, the third phycobiliprotein is the same as the first phycobiliprotein or the second phycobiliprotein. In another embodiment, the third phycobiliprotein is different from the first phycobiliprotein or the second phycobiliprotein and the third phycobiliprotein contains non-crosslinked subunits that exchange with the non-crosslinked subunits of the first and second phycobiliprotein.

In yet a further aspect, the above-described composition containing the first ligand conjugated to the first tandem dye and the unconjugated second phycobiliprotein also includes (a) a second ligand conjugated to a second tandem dye and (b) an unconjugated fourth phycobiliprotein. The second tandem dye includes a third phycobiliprotein and a second partner dye conjugated to the third phycobiliprotein. The third phycobiliprotein contains crosslinked and non-crosslinked subunits and is derived from a second bacterial or eukaryotic algae species. The unconjugated fourth phycobiliprotein contains subunits and is derived from the second bacterial or eukaryotic algae species. In one embodiment, the third and fourth phycobiliproteins are the same. In a further embodiment, the third and fourth phycobiliproteins are different and the fourth phycobiliprotein contains non-crosslinked subunits that exchange with the non-crosslinked subunits of the third phycobiliprotein.

In a further aspect, a method for analyzing cellular and non-cellular populations in a specimen is provided. The method includes combining the specimen and a composition described herein and identifying the populations in the specimen by analyzing fluorescence. Desirably, at least one of the cellular and non-cellular populations includes receptors for the first ligand.

Other aspects and advantages of various embodiments of the invention of the claims are disclosed in the following detailed description thereof.

BRIEF DESCRIPTION OF THE DRAWINGS

FIGS. 1A-3J are dual parameter histograms of two and three-color reagent compositions in which fluorescence intensities of two different fluorochromes are plotted for various cellular populations of the same whole blood specimen. These histograms demonstrate the enhanced stability of the ligand-dye compositions described herein during storage using different amounts of free phycobiliprotein.

FIG. 1A provides a dual parameter histogram of a specimen prepared using, and demonstrating the effects of, a reagent composition available in the prior art containing a ligand/dye conjugate, i.e., CD3-allophycocyanin (APC) (0.5 µg) and a ligand/tandem dye conjugate, i.e., CD19-APC-AlexaFluor®750 tandem dye (0.5 µg), i.e., the "prior art fresh mixture", freshly formulated from components individually stored at 2 to 8° C. for 21 days. The APC in both conjugates is from the same bacterial species, i.e., *Spirulina platensis*. No free (unconjugated) APC is present.

FIGS. 1A and 1B are contrasted with FIGS. 1C and 1D.

FIGS. 3A-3J are dual parameter histograms obtained by using a three-color reagent composition in which fluorescence intensities of two different fluorochromes are plotted for various cellular populations of the same whole blood specimen.

FIGS. 3A and 3B provide the fluorescence histograms of a freshly prepared specimen using a composition of the prior art containing CD4-XL-4-APC-AlexaFluor®700 tandem dye, CD19-APC and the CD8-XL-APC-AlexaFluor®750 tandem dye, i.e., the "prior art fresh mixtures". These histograms are provided for comparison with those of FIGS. 3E-3J.

FIGS. 3C and 3D provide the fluorescence histograms of a specimen using a composition of the prior art containing CD4-XL-4-APC-AlexaFluor®700 tandem dye, CD19-APC and the CD8-XL-APC-AlexaFluor®750 tandem and retained at 2 to 8° C. for 120 days, i.e., the "prior art stored mixtures". These histograms are provided for comparison with those of FIGS. 3E-3J.

FIGS. 3E and 3F provide the fluorescence histograms of a specimen using a composition as described herein containing CD4-XL-4-APC-AlexaFluor®700 tandem dye, CD19-APC and the CD8-XL-APC-AlexaFluor®750 tandem and 0.5 µg of native, unconjugated APC and retained at 2 to 8° C. for 120 days.

FIGS. 3G and 3H provide the fluorescence histograms of a specimen using a composition as described herein containing CD4-XL-4-APC-AlexaFluor®700 tandem dye, CD19-APC and the CD8-XL-APC-AlexaFluor®750 tandem and 1.0 µg of native, unconjugated APC and retained at 2 to 8° C. for 120 days.

FIGS. 3I and 3J provide the fluorescence histograms of a specimen using a composition as described herein containing CD4-XL-4-APC-AlexaFluor®700 tandem dye, CD19-APC and the CD8-XL-APC-AlexaFluor®750 tandem dye and 2.0 µg of native, unconjugated APC and retained at 2 to 8° C. for 120 days.

DETAILED DESCRIPTION OF THE INVENTION

The compositions and methods described herein provide solutions to the difficulties associated with the degradation or instability of phycobiliprotein-containing tandem dyes in multicolor reagent formulations.

The inventors of the present application identified this problem after using compositions containing conjugates of different antibodies to phycobiliproteins and their tandem dyes which had been stored together. Specifically, the "difficulties" described above were observed when conjugates of allophycocyanin (APC) and APC-tandem dyes (e.g., APC.AlexaFluor®700, APC.AlexaFluor®750, APC.Cy®7, etc.) which were conjugated to different antibodies were stored together in a multicolor formulation, combined with a biological specimen, and the sample was thereafter analyzed using flow cytometry. A progressive increase in compensation requirement (bleed-over) was observed in the fluorescence histograms, as compared to the fluorescence histograms using a fresh mix of the same reagents stored separately under otherwise identical conditions. Similar observations were also made when antibody conjugates of phycoerythrin (PE) and PE based tandem dyes (e.g. PE-Texas Red™, PECy®5, PECy®5.5, PE-AlexaFluor®647, PE-AlexaFluor®700 and PECy®7) were used.

Without wishing to be bound by theory, the inventors speculated that subunit exchange that occurs between a ligand-tandem dye conjugate containing a phycobiliprotein and a ligand-phycobiliprotein conjugate, when the same are in admixture, results in an unwanted increase in compensation requirement (bleed-over) between the tandem dye and the directly conjugated phycobiliprotein. The inventors observed that when conjugates of a crosslinked phycobiliprotein, e.g., XL.APC, and a corresponding conjugate of a crosslinked tandem dye, e.g., XL.APC-AlexaFluor®750, were combined and held at temperatures of about 2 to about 8° C., the subunits of the individual phycobiliprotein molecules appeared to exchange. By way of example, the inventors observed that when CD3-APC was mixed with CD19-APC-AlexaFluor®750 and retained at about 2 to about 8° C. over time, CD3-APC-AlexaFluor®750 and CD19-APC conjugates appeared to have been formed as evidenced by fluorescence histograms.

Figure 5:
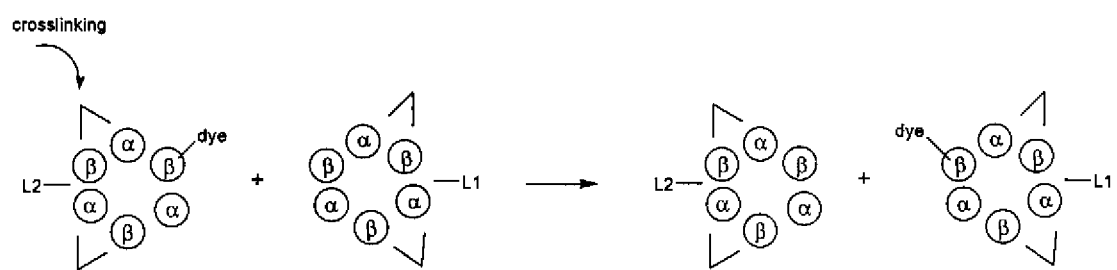
FIG. 5 is a schematic diagram showing subunit exchange that occurs when ligands labeled with a tandem dye comprising a phycobiliprotein and a fluorescable dye are stored together with ligands labeled directly with a phycobiliprotein over time. The brackets (⌒) represent crosslinking, L1 represents a first ligand, L2 represents a second ligand, "dye" represents a fluorescable dye, "α" represents one subunit of the phycobiliprotein, and "β" represents a second subunit of the phycobiliprotein. The term "crosslinking" or variations thereof refers to the connection of molecular units via covalent bonds that are not readily broken.

One aspect of this phycobiliprotein subunit exchange is demonstrated pictorially in FIG. 5. Of course, one of skill in the art would understand that one or more of the ligands and/or fluorescable dyes shown in the schematic of FIG. 5 may be conjugated to crosslinked or non-crosslinked subunits and that various modifications of this subunit exchange can occur in the same solution.

Subunit exchange between allophycocyanin B (APC-B) and allophycocyanin (APC), both isolated from *Synechococcus* 6301, a cyanobacterium, has been discussed in the literature (See, Journal of Biological Chemistry, 256, 12600 (1981)). In summary, it was noted that in mixtures of APC-B and APC, heterologous trimers are formed in near statistical amounts by subunit exchange. For example, APC is known to have a quaternary structure comprising three α-subunits and three β-subunits associated through a combination of hydrophobic interactions as well as hydrogen and ionic bonds based on the structure and amino acid sequence of the individual subunits. APC is also known to dissociate into its subunits (α-β monomers as well as α and β components) at low concentrations, at low pH conditions, and when exposed to one or more chaotropic ions. The term "chaotropic ion" as used herein refers to an agent which disrupts the three dimensional structure of a phycobiliprotein by interfering with stabilizing intra-molecular interactions. Crosslinked APC compositions are reported and are marketed by various commercial vendors (Prozyme Inc. and Martek Biosciences, among others).

The inventors devised the novel reagent compositions discussed herein to address this problem of unwanted subunit exchange. The inventors' discovered that the addition of unconjugated phycobiliprotein, which was from the same bacterial species as the phycobiliprotein in the ligand conjugated tandem dye or able to exchange subunits therewith, to a reagent composition which contained the ligand-conjugated phycobiliprotein tandem dye resulted in relatively stable reagent compositions. Various embodiments of these stable dye compositions as mentioned above in the Summary and discussed in detail below solve the stability problem identified by the inventors for prior art multicolor compositions for analysis of biological specimens. The various embodiments of compositions described herein can contain the following labeled ligands (a) at least one ligand conjugated to a tandem dye that contains a phycobiliprotein; (b) optionally one or more ligand conjugated directly to a phycobiliprotein; and (c) optionally one or more ligand conjugated to a fluorescent dye or label that is not a phycobiliprotein. The compositions also contain as another component at least one unconjugated phycobiliprotein that exchanges subunits with the phycobiliprotein of the ligand conjugated to the tandem dye.

The term "stable" as used herein refers to the compositions of the invention prior and/or subsequent to mixing with a biological specimen. In one embodiment, "stable" refers to the composition described herein which does not result in significant variations in fluorescence properties when added to a biological specimen which is subsequently analyzed for cell populations using fluorescence. Desirably, "stable" refers to the composition in which the fluorescence properties of the ligand-conjugated tandem dye and any other ligand conjugated phycobiliprotein do not vary after being mixed. In a further embodiment, the composition is "stable" immediately after mixing the components thereof and prior to mixing with the biological specimen. In another embodiment, the composition is "stable" after being retained at about 2 to about 8° C. for at least 1 up to about 52 weeks after admixture. As additional examples, such compositions are stable for at least 4, 10, 15, 20, 25, 30, 35, 40, 45, 50, or 51 weeks after admixture.

Desirably, the composition is stable at any temperature required for their storage or usage. In one embodiment, the composition is stable at reduced temperatures, i.e., temperatures less than room temperature. In another embodiment, the composition is stable at about 2 to about 10° C. In specific embodiments, the composition is stable at about 2, 3, 4, 5, 6, 7, 8, 9, or 10° C. In yet another embodiment, the composition is stable at room temperature. In still a further embodiment, the composition is stable at elevated temperatures, i.e., temperatures above room temperature.

When the novel dye compositions described herein were utilized in methods for cellular and non-cellular analysis, reduced or no bleedover relative to a freshly prepared composition was observed in the fluorescence properties of cells labeled with either the ligand-conjugated tandem dye or the ligand-conjugated phycobiliprotein. See, for example, the figures and examples provided herein. Further, the dye compositions resulted in a reduction of erroneous data, reduced costs due to less wasted dye compositions, and a reduction of time required to continually prepare fresh dye compositions, including fresh control compositions.

I. Definitions

The following definitions are provided and include information that is widely available in the art. Where examples of a certain term are provided, the same are not intended to be exhaustive and may include other examples known or available in the art. Therefore, such examples are not meant to be a limitation of the invention.

A. The "Specimen"

A "specimen" as utilized herein is any mammalian cell-containing suspension, i.e., biological specimen, which contains cellular and/or non-cellular populations. In a specific embodiment, the mammal providing the specimen is a human, although specimens from other non-human mammals may also be employed. The terms "cellular" and "non-cellular" are readily understood by one of skill in the art. At least one of the cellular or non-cellular populations requires a receptor for each different ligand utilized in the composition described above. Typical "cellular" populations include, without limitation, hematological cells and non-hematological cells. Such a specimen includes, without limitation, whole blood, peripheral blood, bone marrow aspirate, lymph node tissue, splenic tissue, cerebrospinal fluid, skin tissue, mucosal tissue, thoracentesis fluids, pleural fluids, and spinal fluid. Hematological (i.e., blood) cell populations are selected from among monocytes, lymphocytes, neutrophils, eosinophils, basophils, myelocytes, metamyelocytes, promyelocytes, immature granulocytes, bands, blast cells, variant lymphocytes and atypical lymphocytes. Non-leukocyte hematological cell populations include red blood cells, reticulated red blood cells, nucleated red blood cells, platelets, reticulated platelets and megakaryocytes. In the blood, atypical cells include myelocytes, metamyelocytes, promyelocytes, immature granulocytes, band cells, blast cells, atypical lymphocytes, variant lymphocytes nucleated red blood cells, giant platelets, plasma cells, etc. Non-hematological cells include epithelial cells and endothelial cells, among others. Typical "non-cellular" populations include, without limitation, beads, proteins, microparticles, microsomes, among others.

In one embodiment, the specimen is human whole blood or peripheral blood specimen containing five "normal" leukocyte populations, which are monocytes, lymphocytes, neutrophils, eosinophils, and basophils, as well as possibly a number of atypical cell populations due to disease, reaction to adverse environmental stimuli, e.g., a carcinogen, or a result of therapeutic treatment. Thus, suitable specimens for analysis by these methods are human patient blood specimens, which may likely contain both mature and immature leukocyte cells and non-leukocyte populations, as well as atypical cells. In one example, a specimen contains blast cells. In a further example, a specimen contains nucleated red blood cells. As another example, a specimen contains immature granulocytes. As yet another example, a specimen contains atypical lymphocytes. Other combinations of cells in abnormal specimens may also be analyzed by the methods and compositions described herein.

B. The "Ligand"

In all embodiments of the compositions described herein, the term "ligand" refers to a moiety (e.g., an antibody) that binds to a receptor present on the surface of a cell or a non-cellular particle. In one embodiment, the ligand is "conjugated to", "associated with" or "bound to" a phycobiliprotein of the tandem dye described above. One of skill in the art would readily be able to conjugate a tandem dye to a ligand, such as a monoclonal antibody, by methods in the art. In one embodiment, the tandem dye is conjugated to the ligand by iminothiolane activation of the dye.

As defined herein, ligands include various agents that detect and react with one or more specific receptors. All suitable ligands are characterized by the desired ability to bind the specified receptor on a population of particles. In one embodiment, the ligand is a component that preferentially binds to all or a portion of a cell surface receptor. Typically, the ligand contains an amino acid sequence or nucleic acid sequence, which may be isolated and naturally occurring or recombinantly produced or artificial or synthetic. In one embodiment, the ligand is a protein, such as an antibody or enzyme, or fragment thereof. In another embodiment, the ligand is a nucleic acid probe. In still other embodiments, the ligand is a multimolecular assembly, e.g., a tetramer of a recombinant protein. Methods useful for construction of such ligands are known to those of skill in the art.

Conventionally for cellular analyses, antibodies or antibody fragments directed to cell surface determinants are the ligands of choice. The term "antibody" as used herein is intended to encompass a polyclonal, monoclonal, synthetic or recombinant antibody of classes IgG, IgM, IgA, IgD and IgE. Antibody fragments are also useful and include, without limitation, a Fab fragment, a Fab' fragment, a F(ab')$^2$ fragment or a Fc antibody fragment of one or more of the above intact antibodies. Similarly a single chain variable antibody fragment or a recombinant construct comprising a complementarity determining region (CDR) of an antibody may be employed as the ligands useful in these methods. Further, a synthetic antibody or chimeric antibody or humanized antibody construct which shares sufficient CDRs to retain functionally equivalent binding characteristics of an antibody that binds a desired cell surface antigen may also be employed as the ligand of choice.

In one embodiment, the individual ligands or antibodies for use within the compositions described herein each bind an antigenic determinant that is differentially expressed on populations of cells in the selected specimen, and are chosen so that a particular combination in conjunction with light scatter and/or electrical parameters provides the desired differential information. For example, in one embodiment an antibody useful herein binds to an antigenic determinant that is differentially expressed on populations of leukocytes and non-leukocytes. Such an antigenic determinant may be completely absent from non-leukocytes and expressed only on leukocytes. Alternatively, such an antigenic determinant may be abundantly expressed on leukocytes and minimally expressed on non-leukocytes. Such an antibody thus permits the identification and differentiation of white blood cells from non-white blood cells, such as red blood cells (RBC), nucleated red blood cells or platelets. Still other embodiments employ more than one antibody that binds a different determinant on the same cell type or population. Therefore a combination of different antibodies that bind different determinants on the same cell type or population can be employed in place of a single antibody that binds one determinant on a cell population. In another embodiment, such an antibody (or combination of antibodies) is also capable of differentiating between mature leukocytes and immature leukocytes, based on differential expression of the antigenic determinant on leukocytes as they mature and age.

Antibodies useful as ligands in the compositions described herein and for hematological analyses specifically include, without limitation, anti-CD2, anti-CD3, anti-CD 4, anti-CD5, anti-CD7, anti-CD8, anti-CD9, anti-CD10, anti-CD11a, CD11b, anti-CD13, anti-CD14, anti-CD15, anti-CD16, anti-CD16b, anti-CD18, anti-CD19, anti-CD20, anti-CD23, anti-CD24, anti-CD25, anti-CD33, anti-CD35, anti-CD36, anti-CD38, anti-CD41, anti-CD 45, anti-CD45RA, anti-CD48, anti-CD49d, anti-CD50, anti-CD52, anti-CD53, anti-CD55, anti-CD56, anti-CD59, anti-Cd61, anti-CD62L, anti-CD62p, anti-CD64, anti-CD66b, anti-CD66c, anti-CD73, anti-CD82, anti-CD87, anti-CD90, anti-CD117, anti-CD142, anti-CD235a, anti-CD235b, anti-CD235c, anti-CD236, anti-CD236r, anti-CD239, anti-CD240, anti-CD241, anti-CD242, anti-gp42, anti-LY-6, anti-RT-6, anti-SCA-2, anti-Kappa, anti-Lambda, and anti-HLA-DR, among others known to the art. It will be readily understood that this invention is not limited by the selection of the specific ligand(s) in the composition and that other ligands or antibodies not specifically recited herein could be selected and utilized by one of skill in the art for inclusion in the compositions.

The compositions contain one or more ligand. In one embodiment, the composition contains two or more ligands. In another embodiment, the composition contains three or more ligands. In a further embodiment, the composition contains four or more ligands. In yet another embodiment, the composition contains 1, 2, 3, 4, 5, 6, 7, 8, 9, or 10 ligands. One of skill in the art would readily understand that there is no "maximum" number of ligands that can be utilized in a single reagent composition and that the selection thereof would depend on the capabilities of the reagents and instruments utilized.

The ligands present in a single composition may be the same or may differ. In one embodiment, the composition contains two ligands and the ligands are the same (L1 and L1). In another embodiment, the composition contains two ligands and the ligands are different (L1 and L2). In a further embodiment, the composition contains three ligands and all of the ligands are the same (L1, L1, and L1). In yet a further embodiment, the composition contains three ligands and all three of the ligands are different (L1, L2, and L3). In still another embodiment, the composition contains three ligands and two of the ligands are the same and one ligand is different (L1, L1, and L2). In a further embodiment, the composition contains four ligands and all of the ligands are the same (L1, L1, L1, L1). In yet a further embodiment, the composition contains four ligands and all four of the ligands are different (L1, L2, L3, L4). In still another embodiment, the composition contains four ligands and any two of the ligands are the same and the other two ligands are the same, but differ from the first two ligands (L1, L1, L2, and L2). In yet a further embodiment, the composition contains four ligands and any three of the ligands are the same and the fourth ligand is different (L1, L1, L1, and L2). A similar progression may be utilized to compositions containing five or more ligands and would readily be able to be determined by one of skill in the art. See the following equation, wherein n is the total number of ligands, r is the number of ligands that differ from the others, and $0 \leq r \leq n$.

$$_nC_r = \frac{n!}{r!(n-r)!}$$

Each ligand selected for use in a composition or method described herein is associated with, conjugated to, or bound to a fluorescent detectable label, called a fluorochrome or fluorescent dye. Among such fluorochromes or fluorescent dyes are phycobiliproteins, tandem dyes employing phycobiliproteins conjugated to a partner dye that may or may not be a phycobiliprotein, as well as other dyes conventionally employed to label ligands. In all of the embodiments of the compositions described herein, at least one ligand is conjugated to a tandem dye containing a phycobiliprotein. In other embodiments, additionally at least one phycobiliprotein or other fluorescent dye is bound directly to the ligand.

Methods for associating, conjugating, or coupling the ligand with a selected fluorochrome are similarly conventional and known to those of skill in the art. Known methods of fluorochrome attachment are described (see, for example, Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, Ill., 1994/1995); U.S. Pat. Nos. 6,692,968 and 5,164,311, among others, which are hereby incorporated by reference. Thus, selection of the coupling methods of the tandem dye or phycobiliprotein or other non-phycobiliprotein dye does not limit the compositions described herein. Similarly methods of conjugating the components of a tandem dye are conventional and known to the art.

Optimal concentrations of ligands used in the methods are defined based upon ligand selected and may be determined by the person of skill in the art.

C. The "Tandem Dye"

In all of the embodiments of the compositions described herein, at least one ligand is conjugated to a tandem dye containing a phycobiliprotein. The term "tandem dye", as known to those skilled in the art and used herein, refers to a non-naturally occurring molecule formed of a phycobiliprotein having some degree of crosslinking between its subunits conjugated to another fluorescent dye, referred to herein as a "partner" dye. A variety of known and commercially available tandem dyes may be utilized in the presently described compositions.

Examples of tandem dyes useful in the compositions herein are described in U.S. Pat. Nos. 4,542,104; 5,272,257; and 5,171,846; A. S. Waggoner et al, 1993 *Ann. N.Y. Acad. Sci.*, 677:185-193; M. Roederer et al, 1996 *Cytometry*, 24:191-197, which are hereby incorporated by reference. In one desirable embodiment, the tandem dye is a tandem dye of allophycocyanin and the AlexaFluor® 700 dye, a tandem dye of allophycocyanin and the AlexaFluor® 750 dye, a tandem dye of allophycocyanin and the Cy® 7 dye, a tandem dye of phycoerythrin and the Texas Red™ dye, a tandem dye of phycoerythrin and the Cy® 5 dye, a tandem dye of phycoerythrin and the Cy® 5.5 dye, a tandem dye of phycoerythrin and the Cy® 7 dye, and a tandem dye of allophycocyanin and the H7™ dye.

In one specific embodiment, the tandem dye is APC.AlexaFluor® 700 dye. In another specific embodiment, the tandem dye is APC.AlexaFluor® 750 dye. In yet another specific embodiment, the tandem dye is APC.Cy® 7 dye.

D. "Phycobiliprotein"

Phycobiliproteins, as known to those of skill in the art and used herein, are fluorescent proteins formed of two or more linked subunits that are isolated from bacteria or eukaryotic algae and have been extensively utilized in hematologic analysis. See, "Phycobiliproteins", Robert MacColl and Deborah Guard-Friar, CRS Press (1987), which is hereby incorporated by reference. Phycobiliproteins are widely available in the art from commercial vendors including, without limitation, Invitrogen/Molecular Probes, Pierce (Thermo Fisher Scientific), Sigma, and Prozyme, among others.

In one embodiment, the phycobiliprotein may be isolated from a bacterial species. Certain phycobiliproteins are isolated from a cyanobacterium. Examples of cyanobacterial species that are capable of expressing a phycobiliprotein include, without limitation, *Spirulina platensis, Anabaena variabilis, Gloeobacter violaceus, Tolypothrix tenuis,* or *Lyngbya lagerheimii*. In a further embodiment, the phycobiliprotein may be isolated from a eukaryotic algae species.

In one embodiment, the phycobiliprotein is, without limitation, an allophycocyanin (APC), phycoerythrin (PE), phycocyanin (PC), and phycoerythrocyanin (PEC). In a further embodiment, the phycobiliprotein is R-phycoerythrin (RPE), B-phycoerythrin (BPE), C-phycoerythrin (CPE), Y-phycoerythrin (YPE), C-phycocyanin (CPC), phycoerythrin 566 (PE566), phycoerythrocyanin (PEC), R-phycocyanin (RPC), and allophycocyanin (APC). In another embodiment, the phycobiliprotein is allophycocyanin.

E. The Fluorescent Dye or Fluorochrome

As used herein, any dye described as a "partner" to be conjugated to a phycobiliprotein, as just described, to form a tandem dye, may also be employed in embodiments of the compositions that contain one or more ligands conjugated directly to a non-phycobiliprotein dye. Thus, the following description of fluorochromes, fluorescent labels, or fluorescent dyes other than phycobiliproteins applies to both the tandem partner dye (which is generally other than a phycobiliprotein) and to individual dyes conjugated directly to optional ligand components of these compositions. In certain embodiments of these compositions and methods, at least one phycobiliprotein or other fluorescent dye is bound directly to a ligand. Desirable characteristics of a donor-acceptor pair for tandem dyes are described in U.S. Pat. No. 4,542,104, which is hereby incorporated by reference.

Each fluorescent dye has a characteristic "emission spectrum", of which a portion is a characteristic "peak emission spectrum". As used herein the term "emission spectrum" means generally the amount of electromagnetic radiation of each frequency a fluorochrome emits when it is excited. Generally, an emission spectrum is a range or profile formed by bands of certain frequency, usually measured in nanometers (i.e., wavelength). As used herein, the term "peak emission spectrum" means the most intense portion of the emission spectrum. Emission spectra for a wide variety of dyes are known in the art and published in a variety of well-known texts including, without limitation, Shapiro, Howard M. (2003) Practical Flow Cytometry $4^{th}$ edition, Wiley-Liss, Hoboken, N.J. pp. 296-297, which is hereby incorporated by reference. The peak emission spectrum for any given fluorochrome is known and readily obtained from publications describing such fluorochromes, such as Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, Ill., 1994/1995) Molecular Probes, and other similar texts known to those of skill in the art and incorporated herein by reference. The emission spectral characteristics for any given fluorochrome may also be obtained by performing a spectral scan using a fluorescence spectrophotometer.

Any number of additional, and conventionally employed, fluorescent dyes may be readily selected by one of skill in the art as the "partner" dye of the tandem dye or as a dye to be conjugated directly to a ligand. The partner and other dyes may be readily obtained from commercially sources such as, Sigma-Aldrich, GE Healthcare, Molecular Probes, Inc., Eugene, Oreg. and Prozyme, Inc., San Leandro, Calif. The partner dyes are commercially available, and their uses are known to the art.

Still other fluorescent dyes may be available from other sources or may be developed in the future. Such fluorescent dyes or fluorochromes are anticipated to be useful in these various methods in the same manner as is the exemplary fluorescent dyes of the examples below. These lists of fluorochromes provided below are representative only and do not attempt to include an exhaustive list of dyes suitable for use as "partner" dyes or as dyes directly conjugated to a ligand in one of the embodiments of the compositions and methods. One of skill in the art should be readily able to select the appropriate fluorochrome combinations for use in the compositions and methods described herein in view of the additional teachings of this specification.

The fluorescent dye from which the partner or other dye may be cell permeant or non-cell permeant. By the term "cell permeant" is meant to describe a dye that readily penetrates a cell membrane and stains the components of the cell without requiring the additional presence of a permeabilizing agent in the composition or reaction mixture. In another embodiment, the fluorescent dye from which the partner or other dye may be selected is a cell-impermeant dye, such as those cell-impermeant dyes within the red, green or blue-excited wavelength regions.

Examples of fluorescent "partner" dyes that may be utilized in a tandem dye herein or dyes that may be directly conjugated to a ligand in certain embodiments include, without limitation, the cyanine dyes such as Cy® 5 dye, Cy® 5.5 dye, and Cy® 7 dye; the AlexaFluor® dyes such as the AlexaFluor® 405 dye, AlexaFluor® 610 dye, AlexaFluor® 595 dye, AlexaFluor® 647 dye, AlexaFluor® 700 dye, and AlexaFluor® 750 dye, and the AlexaFluor® 488 dye; Rhodamine 123; Texas Red™ dyes; and Atto™ dyes. Many of these dyes, as well as others that can be utilized as tandem "partner" dyes or as dyes for direct conjugation to the ligand(s) in the methods described herein, are commercially available from Molecular Probes Inc. (Eugene, Oreg.). See, U.S. Pat. No. 5,563,070, which is hereby incorporated by reference.

In one specific embodiment, the fluorescent partner dye is selected from the Texas Red™ dyes, AlexaFluor® dyes, cyanine dyes, and Atto™ dyes. In another specific embodiment, the AlexaFluor® dye is selected from among AlexaFluor® 610 dye, AlexaFluor® 595 dye, AlexaFluor® 647 dye, AlexaFluor® 700 dye, and AlexaFluor® 750 dye. In a further specific embodiment, the cyanine dye is selected from the Cy® 5 dye, Cy® 5.5 dye, and Cy® 7 dye.

II. The Phycobiliprotein Containing Compositions

As discussed above, the compositions provided herein contain in the simplest embodiment a ligand conjugated to a phycobiliprotein-containing tandem dye, and an unconjugated phycobiliprotein.

A. The Tandem Dye Containing a Phycobiliprotein Conjugated to a Partner Dye

The phycobiliprotein component of the tandem dye may be selected from any of the phycobiliproteins set forth above, any phycobiliproteins that are commercially available and any phycobiliproteins that may be prepared or purified by conventional methods. Any phycobiliprotein that contains some crosslinked subunits (and optionally uncrosslinked subunits as well) or is modified to contain crosslinking may be utilized in the tandem dye of the compositions and methods described herein.

In an effort to determine the degree of crosslinking in APC available in the art from commercial vendors, the inventors utilized techniques known in the art including, without limitation, high performance liquid chromatography (HPLC). Further, one of skill in the art would readily be able to perform known purification and crosslinking techniques on APC available from commercial vendors to obtain phycobiliproteins having consistent or higher crosslinking than available from commercial sources. Such methods of purifying or obtaining higher cross-linked phycobiliproteins are known to those of skill in the art. Such conventional methods include Trinquet E., Maurin F., Préaudat M., Mathis G. (2001) "Allophycocyanin I as a Near Infrared Fluorescent: Isolation, Characterization, Chemical Modification, and Use in a Homogeneous Fluorescence Resonance Energy Transfer System", Analyt. Biochem. 296, 232-244.

In one embodiment, the phycobiliprotein component of the tandem dye contains at least about 20, 25, 30, 35, 40, 45, 50, 55, 60, 65, 70, 75, 76, 80, 85, 90, 91, 92, 93, 94, 95, 96, 97, 98, 99, or 100%, or fractional percentages therebetween, of crosslinking. In another embodiment, the phycobiliprotein component of the tandem dye contains about 50% to about 100% crosslinking. In a further embodiment, the phycobiliprotein component of the tandem dye contains about 60% to about 100% crosslinking. In still another embodiment, the phycobiliprotein component of the tandem dye contains about 70% to about 100% crosslinking. In yet a further embodiment, the phycobiliprotein component of the tandem dye contains about 80% to about 100% crosslinking. In yet another embodiment, the phycobiliprotein component of the tandem dye contains about 90% to about 100% crosslinking. In still a further embodiment, the phycobiliprotein component of the tandem dye contains about 95% to about 100% crosslinking. However, it is not a limitation of the invention if the phycobiliprotein component of the tandem dyes has crosslinking of less than 20%.

The fluorescent "partner" dye which is conjugated to the phycobiliprotein to form a tandem dye may be selected from dyes described above. According to various embodiments of the methods and compositions described herein, the dye used as the partner dyes in a tandem dye that is conjugated to a ligand or ligands may also be used in a tandem dye with another phycobiliprotein, or used to independently label a ligand in the compositions.

B. Unconjugated Phycobiliprotein

In addition to the labeled ligands discussed above, embodiments of the compositions described herein also require the presence of unconjugated phycobiliprotein. An "unconjugated" or "free" phycobiliprotein as used herein is a phycobiliprotein as described above, but is not conjugated to a ligand. The unconjugated phycobiliprotein contains subunits, whereby some of the subunits must not be crosslinked. In one embodiment, the unconjugated phycobiliprotein contains no crosslinking between its subunits. In another embodiment, the unconjugated phycobiliprotein contains crosslinking between the subunits. If crosslinking is present in the unconjugated phycobiliprotein, it is desirable that the amount of crosslinking in the unconjugated phycobiliprotein is less than the amount of crosslinking in the conjugated phycobiliprotein of the tandem dye.

In one embodiment, the unconjugated phycobiliprotein must be derived from the same bacterial or eukaryotic algae species as the conjugated phycobiliprotein of the tandem dye. For best results, for each ligand conjugated tandem dye, a corresponding unconjugated phycobiliprotein (derived from the same species as the phycobiliprotein in the tandem dye) must be added to the composition. In one embodiment, the unconjugated phycobiliprotein is the same as the conjugated phycobiliprotein. The term "same", when used to describe the conjugated and unconjugated phycobiliproteins refers to the identical structural characteristics of each molecule.

In another embodiment, the unconjugated phycobiliprotein is different than the conjugated phycobiliprotein of the tandem dye, but the unconjugated phycobiliprotein contains non-crosslinked subunits that exchange with the non-crosslinked subunits of the phycobiliprotein of the tandem dye.

The unconjugated phycobiliprotein may also be purchased from the commercial vendors set forth above or may be an isolated, native protein, a synthetic protein, or a modified protein, as described above. The source of the phycobiliprotein or the amount of modifications made thereto for use herein, however, is not a limitation of the present invention. The unconjugated phycobiliprotein may also be altered or modified to eliminate or diminish its fluorescence. In one embodiment, the unconjugated phycobiliprotein is photobleached, e.g., by irradiation with UV light. In another embodiment the phycobiliprotein may be chemically bleached, i.e., by using 1-3% Clorox® reagent. One of skill in the art would readily be able to modify an unconjugated phycobiliprotein for use herein using standard methodologies in the art.

The amount of unconjugated phycobiliprotein required in the composition is that which is sufficient to stabilize the composition. Desirably, the unconjugated phycobiliprotein is present in an amount which permits exchange of non-crosslinked subunits at a steady state. In one embodiment, the ratio of the unconjugated phycobiliprotein to the conjugated phycobiliprotein of the tandem dye is at least 0.125:1, 0.25:1, 0.50:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1, and fractional ratios therebetween. In another embodiment, the ratio of the unconjugated phycobiliprotein to the conjugated phycobiliprotein is about 0.125:1 to about 20:1. In yet another embodiment, the ratio of the unconjugated phycobiliprotein to the conjugated phycobiliprotein is about 0.25:1 to about 10:1. In a further embodiment, the ratio of the unconjugated phycobiliprotein to the conjugated phycobiliprotein is 4:1 to 0.25:1.

In one embodiment, the conjugated phycobiliprotein of the tandem dye and unconjugated phycobiliproteins are the same and are allophycocyanin, phycoerythrin, phycocyanin, or phycoerythrocyanin. In another embodiment, the conjugated phycobiliprotein of the tandem dye and unconjugated phycobiliproteins are different. However, if the conjugated phycobiliprotein of the tandem dye and unconjugated phycobiliprotein are different, they must contain non-crosslinked subunits that exchange with each other. For example, the conjugated phycobiliprotein of the tandem dye and unconjugated phycobiliprotein are different, are, independently, allophycocyanin, phycoerythrin, phycocyanin, or phycoerythrocyanin, and contain non-crosslinked subunits that exchange with each other. In a further embodiment, the conjugated phycobiliprotein of the tandem dye and unconjugated phycobiliprotein are the same and are APC, R-PE, B-PE, C-PE, Y-PE, or PEC. In still a further embodiment, the conjugated phycobiliprotein of the tandem dye and unconjugated phycobiliproteins are different, are, independently, APC, R-PE, B-PE, C-PE, Y-PE, or PEC, and contain non-crosslinked subunits that exchange with each other. In yet another embodiment, the conjugated phycobiliprotein of the tandem dye and unconjugated phycobiliproteins are the same and are R-PE, B-PE, Y-PE, PE566, PEC, R-PC, or APC. In a further embodiment, the conjugated phycobiliprotein of the tandem dye and unconjugated phycobiliproteins are different, are independently selected from R-PE, B-PE, Y-PE, PE566, PEC, R-PC, or APC, and contain non-crosslinked subunits that exchange with each other. In still another embodiment, the conjugated phycobiliprotein of the tandem dye and unconjugated phycobiliproteins are the same and are allophycocyanins. In yet another embodiment, the conjugated phycobiliprotein of the tandem dye and unconjugated phycobiliproteins are the same and are phycoerythrins.

C. Additional Ligand-Conjugated Dye Components in the Composition

In addition to a single phycobiliprotein-containing tandem dye and a single unconjugated phycobiliprotein, other embodiments of dye and ligand-containing compositions can contain multiple ligands, multiple tandem dyes, multiple unconjugated dyes and other optional components. In order to be most useful in enumerating a variety of cell populations, it is advantageous that the dye compositions contain multiple ligand-conjugated fluorescent dyes. The term "additional" as used in the context can readily be determined by one of skill in the art. For example, the term "additional" may include 1, 2, 3, 4, 5, 6, 7, 8, 9, or 10 more components, including ligand-conjugated dye components and unconjugated phycobiliproteins.

Each additional dye or additional phycobiliprotein included in the dye composition must be directly conjugated to one or more ligands of the composition. In most of the compositions described herein, there is no unlabeled or unconjugated ligand in the dye composition.

In one embodiment, the composition of the invention includes one or more additional ligands conjugated to a fluorescent dye or fluorochrome that is not a phycobiliprotein. For example, the dye composition may include x ligands conjugated to y dyes, wherein x=y and are integers. In one embodiment, x and y are 1, 2, 3, 4, 5, 6, 7, 8, 9, or 10. In a further embodiment, x and y are 1, 2, 3, or 4. The dye may be any of the dyes described above. One of skill in the art would readily be able to select a suitable dye for addition to the dye composition.

In another embodiment, the dye composition of the invention includes one or more additional ligands directly conjugated to an additional phycobiliprotein. In one embodiment, the additional phycobiliprotein is from the same bacterial or eukaryotic algae species as the phycobiliprotein of the ligand-conjugated tandem dye in the dye composition.

In another embodiment, the additional phycobiliprotein is from another bacterial or eukaryotic algae species as the phycobiliprotein of the ligand-conjugated tandem dye in the dye composition. For example, the dye composition may include x' ligands conjugated to y' phycobiliproteins, wherein and are integers. In one embodiment, x' and y' are 1, 2, 3, 4, 5, 6, 7, 8, 9, or 10. In a further embodiment, x' and y' are 1, 2, 3, or 4. The phycobiliprotein used to directly label another ligand may be any of the phycobiliproteins described above. In one embodiment, the additional phycobiliprotein does not contain non-crosslinked subunits that exchange with the non-crosslinked subunits of any of the phycobiliproteins in the composition (either the ligand-conjugated tandem dye or the unconjugated phycobiliprotein). In a further embodiment, the additional phycobiliprotein contains non-crosslinked subunits that exchange with non-crosslinked subunits of one or more of the phycobiliproteins in ligand-conjugated tandem dye or the unconjugated phycobiliprotein of the composition. One of skill in the art would readily be able to select a suitable phycobiliprotein for direct conjugation to a ligand and subsequent addition to the reagent mixture.

In still another embodiment, the dye composition of the invention includes one or more additional ligands conjugated to an additional tandem dye containing an additional phycobiliprotein. For example, the dye composition may include x" ligands, each separately conjugated to y" tandem dyes, wherein x"=y" and are integers. In one embodiment, x" and y" are 1, 2, 3, 4, 5, 6, 7, 8, 9, or 10. In a further embodiment, x" and y" are 1, 2, 3, or 4. In one embodiment, the phycobiliprotein in the additional tandem dye is from the same bacterial or eukaryotic algae species as the phycobiliprotein in the first ligand-conjugated tandem dye composition. In another embodiment, the additional phycobiliprotein is from a bacterial species or eukaryotic algae species different from that of the phycobiliprotein in the first dye composition. However, if the additional phycobiliprotein in the additional tandem dye is from another bacterial or eukaryotic algae species, the same phycobiliprotein in an unconjugated form must be added to the dye composition. However, regardless of the source of the phycobiliprotein, it may be selected by one skilled in the art from any of the phycobiliproteins described above.

A variety of embodiments of compositions contain multiple ligands conjugated to tandem dyes. For example, in one desirable embodiment, the composition may contain in addition to the (a) first ligand conjugated to a first tandem dye and (b) a first unconjugated phycobiliprotein, the following components: (c) a second ligand conjugated to a second tandem dye, the second tandem dye including (i) a third phycobiliprotein that contains crosslinked and non-crosslinked subunits, the third phycobiliprotein derived from a second bacterial or eukaryotic algae species; and (ii) a second partner dye conjugated to the third phycobiliprotein; and (d) an unconjugated fourth phycobiliprotein that contains subunits. The second phycobiliprotein is derived from the second bacterial or eukaryotic algae species. The fourth phycobiliprotein and the third phycobiliprotein are the same. Alternatively, the third and fourth phycobiliproteins are different and the fourth phycobiliprotein contains non-crosslinked subunits that exchange with the non-crosslinked subunits of the third phycobiliprotein.

In another desirable embodiment, the composition may further contain in addition to the components described immediately above: (e) a third ligand conjugated to a fourth phycobiliprotein, the fourth phycobiliprotein derived from the first bacterial species, first eukaryotic algae species, second bacterial species, or the second eukaryotic algae species. The fourth phycobiliprotein is the same as the first, second, or third phycobiliprotein; or alternatively, the fourth phycobiliprotein is different from the first, second, or third phycobiliprotein and contains non-crosslinked subunits that exchange with the non-crosslinked subunits of the first, second, or third phycobiliprotein.

In a further desirable embodiment, the composition may contain in addition to the (a) first ligand conjugated to a first tandem dye and (b) a first unconjugated phycobiliprotein, the following components: (c) a second ligand conjugated to a third phycobiliprotein, the third phycobiliprotein derived from the first bacterial or eukaryotic algae species. The third phycobiliprotein is the same as the first or second phycobiliprotein; or alternatively, the third phycobiliprotein is different from the first or second phycobiliprotein and the third phycobiliprotein contains non-crosslinked subunits that exchange with the non-crosslinked subunits of the first and second phycobiliprotein. In one aspect, the third phycobiliprotein does not contain non-crosslinked subunits that exchange with the non-crosslinked subunits of the first or second phycobiliprotein. In another aspect, the third phycobiliprotein contains non-crosslinked subunits that exchange with non-crosslinked subunits of the first or second phycobiliprotein.

In another desirable embodiment, the composition further contains one or more additional ligands conjugated to a dye that is not a phycobiliprotein.

D. Other Optional Non-Dye Components in the Composition

Components other than additional ligands, phycobiliproteins, tandem dyes, and fluorescent dyes may be included in the compositions described herein. The selection of the additional components may be readily selected by one of skill in the art and will depend on the specimen analyzed, the components of the composition, the parameters analyzed, among others. See, for example, surfactants listed in U.S. Pat. No. 6,551,831, which is hereby incorporated by reference.

An embodiment of a composition may further contain other components, such as buffers that maintain the pH of the composition at any desired pH within the range of about 6 to about 9. Examples of buffers include, without limitation, phosphate buffered saline or isotonic saline, such as ISOTON II buffer (Coulter Corporation, Miami, Fla.) and those identified in U.S. Pat. No. 3,962,125, which is hereby incorporated by reference.

Preservatives can also be added to the compositions and may be selected from, but not limited to, 5-Chloro-2-methyl-4-isothiazolin-3-one, and 2-methyl-4-isothiazolin-3-one (such preservatives may be purchased commercially, e.g., as ProClin® 300 or ProClin® 150).

Selection of an appropriate surfactant, buffer, preservative or other conventional reagent that can be utilized in the compositions for use in the various methods described herein may be made by one of skill in the art. Such selection is not a limitation of the methods and compositions taught herein.

E. Compositions Containing Multiple Labeled Ligands

In one desirable embodiment, the composition contains one ligand conjugated to a tandem dye (L1-tandem dye 1). In another embodiment, the composition contains two ligands in which one antibody is conjugated to a tandem dye (L1-tandem dye 1) and the other ligand is conjugated directly to a phycobiliprotein (L2-pbp). In a further embodiment, the composition contains two ligands in which one ligand is conjugated to one tandem dye (L1-tandem dye 1) and a ligand is conjugated to a second tandem dye (L2-tandem dye 2). In another embodiment, the composition contains three ligands in which one ligand is conjugated to one tandem dye (L1-tandem dye 1), a second ligand is conjugated to a second tandem dye (L2-tandem dye 2), and a third ligand is conjugated to a phycobiliprotein (L3-pbp). In still another embodiment, the composition contains one ligand conjugated to one tandem dye (L1-tandem dye 1), a second ligand conjugated to a phycobiliprotein (L2-pbp), and x number of ligands independently conjugated to x number of tandem dyes ($L_x$-tandem dye x). In a further embodiment, the composition contains one ligand conjugated to one tandem dye (L1-tandem dye 1), a second ligand conjugated to a phycobiliprotein (L2-pbp), and x number of ligands independently conjugated to x number of non-phycobiliprotein fluorescable dyes ($L_x$-$dye_x$).

III. Specific Embodiments of Compositions of the Invention

As a first example of a composition described generally above, a composition contains (a) a first ligand conjugated to a first tandem dye. The first tandem dye includes a first phycobiliprotein that contains crosslinked and non-crosslinked subunits conjugated to a first partner dye conjugated to the first phycobiliprotein. The first phycobiliprotein is derived from a first bacterial or eukaryotic algae species. The composition also contains (b) an unconjugated second phycobiliprotein that contains subunits, which second phycobiliprotein is derived from the first bacterial or eukaryotic algae species. In one embodiment of this composition, the second phycobiliprotein and the first phycobiliprotein are the same. In another embodiment of this composition, the second phycobiliprotein and the first phycobiliprotein are different and the second phycobiliprotein contains non-crosslinked subunits that exchange with the non-crosslinked subunits of the first phycobiliprotein. See, Table 1.

TABLE 1

| Composition Components | Tandem Dye Components |
|---|---|
| ligand-1 conjugated to tandem dye-1 unconjugated phycobiliprotein-2 (species 1) | phycobiliprotein-1 (species 1) conjugated to partner dye-1 |

As a second example or embodiment of a composition described herein, a composition contains (a) a first ligand conjugated to a first tandem dye. The first tandem dye includes a first phycobiliprotein that contains crosslinked and non-crosslinked subunits conjugated to a first partner dye conjugated to the first phycobiliprotein. The first phycobiliprotein is derived from a first bacterial or eukaryotic algae species. The composition also contains (b) an unconjugated second phycobiliprotein that contains subunits, which second phycobiliprotein is derived from the first bacterial or eukaryotic algae species. In one embodiment of this composition, the second phycobiliprotein and the first phycobiliprotein are the same. In another embodiment of this composition, the second phycobiliprotein and the first phycobiliprotein are different and the second phycobiliprotein contains non-crosslinked subunits that exchange with the non-crosslinked subunits of the first phycobiliprotein. This second embodiment of a composition further contains (c) a second ligand conjugated to a second tandem dye, the second tandem dye including (i) a third phycobiliprotein that contains crosslinked and non-crosslinked subunits and (ii) a second partner dye conjugated to the third phycobiliprotein. The third phycobiliprotein is derived from the first bacterial or eukaryotic algae species. In one embodiment of this composition, the first, second, and third phycobiliproteins are the same. In another embodiment of this composition, the third phycobiliprotein is different from the first and second phycobiliproteins and the third phycobiliprotein contains non-crosslinked subunits that exchange with the non-crosslinked subunits of the first and second phycobiliproteins. See, Table 2.

TABLE 2

| Composition Components | Tandem Dye Components |
| --- | --- |
| ligand-1 conjugated to tandem dye-1 unconjugated phycobiliprotein-2 (species 1) | phycobiliprotein-1 (species 1) conjugated to partner dye-1 |
| ligand-2 conjugated to tandem dye-2 | phycobiliprotein-3 (species 1) conjugated to partner dye-2 |

In a further embodiment, a composition contains (a) a first ligand conjugated to a first tandem dye, the first tandem dye including (i) a first phycobiliprotein that contains crosslinked and non-crosslinked subunits, the first phycobiliprotein derived from a first bacterial or eukaryotic algae species; and (ii) a first partner dye conjugated to the first phycobiliprotein;

(b) an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein;

(c) a second ligand conjugated to a second tandem dye, the second tandem dye including a third phycobiliprotein that contains crosslinked and non-crosslinked subunits, the third phycobiliprotein derived from the first bacterial or eukaryotic algae species and conjugated to a second partner dye; wherein, the first, second, and third phycobiliproteins are the same; or the third phycobiliprotein is different from the first and second phycobiliproteins and the third phycobiliprotein contains non-crosslinked subunits that exchange with the non-crosslinked subunits of the first and second phycobiliproteins; and (d) a third ligand conjugated to a third tandem dye, the third tandem dye including a fourth phycobiliprotein that contains crosslinked and non-crosslinked subunits, the fourth phycobiliprotein derived from the first bacterial or eukaryotic algae species and conjugated to a third partner dye; wherein, the first, second, third, and fourth phycobiliproteins are the same; or the fourth phycobiliprotein is different from the first, second, or third phycobiliproteins and the fourth phycobiliprotein contains non-crosslinked subunits that exchange with the non-crosslinked subunits of the first, second, or third phycobiliproteins. See, Table 3.

TABLE 3

| Composition Components | Tandem Dye Components |
| --- | --- |
| ligand-1 conjugated to tandem dye-1 unconjugated phycobiliprotein-2 (species 1) | phycobiliprotein-1 (species 1) conjugated to partner dye-1 |
| ligand-2 conjugated to tandem dye-2 | phycobiliprotein-3 (species 1) conjugated to partner dye-2 |
| ligand-3 conjugated to tandem dye-3 | phycobiliprotein-4 (species 1) conjugated to partner dye-3 |

In still a further embodiment, a composition contains (a) a first ligand conjugated to a first tandem dye, the first tandem dye including (i) a first phycobiliprotein that contains crosslinked and non-crosslinked subunits, the first phycobiliprotein derived from a first bacterial or eukaryotic algae species; and (ii) a first partner dye conjugated to the first phycobiliprotein;

(b) an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein;

(c) a second ligand conjugated to a second tandem dye, the second tandem dye including a third phycobiliprotein that contains crosslinked and non-crosslinked subunits, the third phycobiliprotein derived from the first bacterial or eukaryotic algae species and conjugated to a second partner dye; wherein, the first, second, and third phycobiliproteins are the same; or the third phycobiliprotein is different from the first and second phycobiliproteins and the third phycobiliprotein contains non-crosslinked subunits that exchange with the non-crosslinked subunits of the first and second phycobiliproteins;

(d) a third ligand conjugated to a third tandem dye, the third tandem dye including a fourth phycobiliprotein that contains crosslinked and non-crosslinked subunits, the fourth phycobiliprotein derived from the first bacterial or eukaryotic algae species and conjugated to a third partner dye; wherein, the first, second, third, and fourth phycobiliproteins are the same; or the fourth phycobiliprotein is different from the first, second, or third phycobiliproteins and the fourth phycobiliprotein contains non-crosslinked subunits that exchange with the non-crosslinked subunits of the first, second, or third phycobiliproteins; and (e) a fourth ligand conjugated to a fourth tandem dye, the fourth tandem dye including a fifth phycobiliprotein that comprises crosslinked and non-crosslinked subunits, the fifth phycobiliprotein derived from the bacterial or eukaryotic algae species and conjugated to a fourth partner dye; wherein, the first, second, third, fourth, and fifth phycobiliproteins are the same; or the fifth phycobiliprotein is different from the first, second, third, or fourth phycobiliproteins and the fifth phycobiliprotein contains non-crosslinked subunits that exchange with the non-crosslinked subunits of the first, second, third, or fourth phycobiliproteins. See, Table 4.

TABLE 4

| Composition Components | Tandem Dye Components |
| --- | --- |
| ligand-1 conjugated to tandem dye-1 unconjugated phycobiliprotein-2 (species 1) | phycobiliprotein-1 (species 1) conjugated to partner dye-1 |

TABLE 4-continued

| Composition Components | Tandem Dye Components |
|---|---|
| ligand-2 conjugated to tandem dye-2 | phycobiliprotein-3 (species 1) conjugated to partner dye-2 |
| ligand-3 conjugated to tandem dye-3 | phycobiliprotein-4 (species 1) conjugated to partner dye-3 |
| ligand-4 conjugated to tandem dye-4 | phycobiliprotein-5 (species 1) conjugated to partner dye-4 |

In yet another embodiment, a composition contains (a) a first ligand conjugated to a first tandem dye, the first tandem dye including a first phycobiliprotein that contains crosslinked and non-crosslinked subunits, the first phycobiliprotein derived from a first bacterial or eukaryotic algae species and conjugated to a first partner dye;

(b) an unconjugated second phycobiliprotein that contains subunits, the second phycobiliprotein derived from the first bacterial or first eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein; and (c) one or more additional ligands conjugated to a dye that is not a phycobiliprotein. See, Table 5.

TABLE 5

| Composition Components | Tandem Dye Components |
|---|---|
| ligand-1 conjugated to tandem dye-1 unconjugated phycobiliprotein-2 (species 1) ligand-2 conjugated to non-phycobiliprotein dye-2 | phycobiliprotein-1 (species 1) conjugated to partner dye-1 |

In a further embodiment, a composition is provided and contains:

(a) a first ligand conjugated to a first tandem dye, the first tandem dye including a first phycobiliprotein that contains crosslinked and non-crosslinked subunits, the first phycobiliprotein derived from a first bacterial or eukaryotic algae species and conjugated to a first partner dye;

(b) an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein;

(c) a second ligand conjugated to a second tandem dye, the second tandem dye including a third phycobiliprotein that contains crosslinked and non-crosslinked subunits, the third phycobiliprotein derived from a second bacterial or eukaryotic algae species and conjugated to a second partner dye; and (d) an unconjugated fourth phycobiliprotein that contains subunits, the second phycobiliprotein derived from the second bacterial or eukaryotic algae species; wherein, the fourth phycobiliprotein and the third phycobiliprotein are the same; or the fourth phycobiliprotein and the third phycobiliprotein are different and the fourth phycobiliprotein contains non-crosslinked subunits that exchange with the non-crosslinked subunits of the third phycobiliprotein. See, Table 6.

TABLE 6

| Composition Components | Tandem Dye Components |
|---|---|
| ligand-1 conjugated to tandem dye-1 unconjugated phycobiliprotein-2 (species 1) | phycobiliprotein-1 (species 1) conjugated to partner dye-1 |
| ligand-2 conjugated to tandem dye-2 unconjugated phycobiliprotein-4 (species 2) | phycobiliprotein-3 (species 2) conjugated to partner dye-2 |

In another embodiment, a composition is provided and contains:

(a) a first ligand conjugated to a first tandem dye, the first tandem dye including a first phycobiliprotein that contains crosslinked and non-crosslinked subunits, the first phycobiliprotein derived from a first bacterial or eukaryotic algae species and conjugated to a first partner dye;

(b) an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein;

(c) a second ligand conjugated to a second tandem dye, the second tandem dye including a third phycobiliprotein that contains crosslinked and non-crosslinked subunits, the third phycobiliprotein derived from a second bacterial or eukaryotic algae species and conjugated to a second partner dye;

(d) an unconjugated fourth phycobiliprotein that contains subunits, the second phycobiliprotein derived from the second bacterial or eukaryotic algae species; wherein, the fourth phycobiliprotein and the third phycobiliprotein are the same; or the fourth phycobiliprotein and the third phycobiliprotein are different and the fourth phycobiliprotein contains non-crosslinked subunits that exchange with the non-crosslinked subunits of the third phycobiliprotein; and (e) a third ligand conjugated to a fourth phycobiliprotein, the fourth phycobiliprotein derived from the first bacterial species, the first eukaryotic algae species, the second bacterial species, or the second eukaryotic algae species; wherein, the fourth phycobiliprotein is the same as the first phycobiliprotein, the second phycobiliprotein, or the third phycobiliprotein; or the fourth phycobiliprotein and is different from the first, second, or third phycobiliprotein and contains non-crosslinked subunits that exchange with the non-crosslinked subunits of the first, second, or third phycobiliprotein. See, Table 7.

TABLE 7

| Composition Components | Tandem Dye Components |
|---|---|
| ligand-1 conjugated to tandem dye-1 unconjugated phycobiliprotein-2 (species 1) | phycobiliprotein-1 (species 1) conjugated to partner dye-1 |
| ligand-2 conjugated to tandem dye-2 unconjugated phycobiliprotein-4 (species 2) | phycobiliprotein-3 (species 2) conjugated to partner dye-2 |
| ligand-3 conjugated to phycobiliprotein-3 (species 2) | |

Other compositions may be prepared containing additional components selected by those of skill in the art using the teachings of this specification.

IV. Methods for Preparing and Using the Compositions of the Invention

The methods for preparing the compositions discussed herein generally include combining or premixing the labeled ligand and free phycobiliprotein components of the selected multicolor composition, and optionally storing the premixed composition. The composition is then diluted, if necessary, as determined by one of skill in the art, and combined with the selected biological specimen intended for analysis.

Specifically, the composition is prepared by admixing (a) a first ligand conjugated to a first tandem dye, the first tandem dye including a first phycobiliprotein containing crosslinking and a first dye, the first phycobiliprotein derived from a first bacterial or eukaryotic algae species and conjugated to the first dye; and (b) an unconjugated first phycobiliprotein derived from the first bacterial or eukaryotic algae species. Additional components may be added as described above, depending on the populations to be analyzed. In one embodiment, a second ligand conjugated to a second dye selected from the group consisting of a second phycobiliprotein, a second tandem dye comprising the second phycobiliprotein, and a dye that is not a phycobiliprotein is added to the reaction mixture.

One of skill in the art would be able to determine the amount of composition required for use in the methods described below. In one embodiment, at least about 5, 10, 20, 30, 40, 50, 60, 70, 80, 90, 100, 110, 120, 130, 140, 150, 160, 170, 180, 190, or 200 μl, of the composition is utilized. In another embodiment, about 5 to about 200 μl, of the composition are utilized. In a further embodiment, about 100 μL of composition is used.

These components are generally mixed or reacted by incubating at any selected temperature including room temperature, ambient temperature or at reduced temperatures as low as 2° C. In another embodiment, elevated temperatures of about 40° C. may be utilized. However, the temperature of the composition at the time of analysis must be sufficient for viability of the cells in the specimen. In one embodiment, a temperature of about 2 to about 8° C. may be utilized, particularly for both mixture and storage of the mixtures.

The reaction time range is generally greater than about 15 seconds, 30 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, or 15 minutes, or seconds therebetween. In another embodiment, the incubation time is about 15 seconds to about 30 minutes. In a further embodiment, a faster reaction time can be obtained if the concentrations of the components of the composition are adjusted.

Compositions containing the components described above and as prepared above are useful in conventional methods for analyzing cellular and non-cellular populations in a specimen, as demonstrated by the examples below. Such conventional flow cytometric methods are known to one of skill in the art and include combining the specimen and a composition described herein and identifying the populations in the specimen by analyzing fluorescence. Desirably, at least one of the cellular and non-cellular populations includes receptors for the first ligand. See, U.S. Pat. No. 6,551,831, which is hereby incorporated by reference.

V. Kits of the Invention

In yet another aspect, a kit is provided to enable for admixture or use of these compositions in conventional flow cytometric analyses. Desirably, such kits are employed for performing the flow cytometric diagnostic methods of this invention. However, such kits can be assembled for research purposes in developing and evaluating other stabilizing reagents.

The compositions, the components thereof, as well as components necessary to perform any number of variations of the methods described above may be assembled into a kit for convenient use. Such a kit may contain the components required to form composition as separate components. In one embodiment, one separate component present in a separate container is a first ligand conjugated to a first tandem dye, the first tandem dye including a first phycobiliprotein containing crosslinking and derived from a first bacterial or eukaryotic algae species conjugated to a first dye. A second separate component present in a second container is an unconjugated first phycobiliprotein derived from the first bacterial or eukaryotic algae species. These two components may be combined for use at the purchaser's discretion. In another embodiment, the kit may contain one "pre-mixed" container which includes (a) a first ligand conjugated to a first tandem dye, the first tandem dye including (i) a first phycobiliprotein containing crosslinking, the first phycobiliprotein derived from a first bacterial or eukaryotic algae species and (ii) a first partner dye; and (b) an unconjugated first phycobiliprotein derived from the first bacterial or eukaryotic algae species. As discussed above, it is an advantage of the compositions discussed herein that they do not degrade or have subunit exchange among the separate components that interfere in hematological analysis.

Additional containers may be further included in the kits. These additional containers may independently contain any of the optional components identified above. However, the additional, if any, component(s) must have a physiological pH that does not adversely affect the stability of the reagent composition.

Such a kit may further contain one or more of instructions for mixing the separate components of the composition, suitable vessels containing the components of the composition, suitable vessels for mixing the composition with a biological specimen, suitable controls or tables of normal or disease-characteristic values of cells; an anti-coagulant or coagulation pathway inhibitor, other reagents suitable for the performance of flow cytometric analyses and combinations thereof; suitable diluents and buffers for the specimens, disposable gloves, decontamination instructions, applicator sticks or containers, and preparator cups.

One of skill in the art could assemble any number of kits with the information and components necessary to perform the method on a specimen for analysis.

In one embodiment, a kit is provided and contains (a) a first container which includes a first ligand conjugated to a first tandem dye, the first tandem dye including a first phycobiliprotein that contains crosslinked and non-crosslinked subunits, the first phycobiliprotein derived from a first bacterial or eukaryotic algae species and conjugated to a first partner dye; and (b) a second container which includes an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein. One or more additional containers can be included in the kit and may contain any one of the reagents noted above. See, Table 8. Alternatively, the components of the composition may be present in one container.

TABLE 8

| Container | Container Components | Tandem Dye Components |
|---|---|---|
| 1 | ligand-1 conjugated to tandem dye-1 | phycobiliprotein-1 (species 1) conjugated to partner dye-1 |
| 2 | unconjugated phycobiliprotein-2 (species 1) | |
| 3 or more | optional components recited above | |

In another embodiment, a kit is provided and contains (a) a first container which includes a first ligand conjugated to a first tandem dye, the first tandem dye including a first phycobiliprotein that contains crosslinked and non-crosslinked subunits, the first phycobiliprotein derived from a first bacterial or eukaryotic algae species and conjugated to a first partner dye; (b) a second container which includes an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein; and (c) a third container which includes a second ligand conjugated to a second tandem dye, the second tandem dye including a third phycobiliprotein that contains crosslinked and non-crosslinked subunits, the third phycobiliprotein derived from the first bacterial or eukaryotic algae species and conjugated to a second partner dye; wherein, the first, second, and third phycobiliproteins are the same; or the third phycobiliprotein is different from the first and second phycobiliproteins and the third phycobiliprotein contains non-crosslinked subunits that exchange with the non-crosslinked subunits of the first and second phycobiliproteins. See, Table 9. Alternatively, the components of the composition may be present in one container.

TABLE 9

| Container | Container Components | Tandem Dye Components |
|---|---|---|
| 1 | ligand-1 conjugated to tandem dye-1 | phycobiliprotein-1 (species 1) conjugated to partner dye-1 |
| 2 | unconjugated phycobiliprotein-2 (species 1) | |
| 3 | ligand-2 conjugated to tandem dye-2 | phycobiliprotein-3 (species 1) conjugated to partner dye-2 |
| 4 or more | optional components recited above | |

In a further embodiment, a kit is provided and contains (a) a first container which includes a first ligand conjugated to a first tandem dye, the first tandem dye including a first phycobiliprotein that contains crosslinked and non-crosslinked subunits, the first phycobiliprotein derived from a first bacterial or eukaryotic algae species and conjugated to a first partner dye; (b) a second container which includes an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein; (c) a third container which includes a second ligand conjugated to a second tandem dye, the second tandem dye including a third phycobiliprotein that contains crosslinked and non-crosslinked subunits, the third phycobiliprotein derived from the first bacterial or eukaryotic algae species and conjugated to a second partner dye; wherein, the first, second, and third phycobiliproteins are the same; or the third phycobiliprotein is different from the first and second phycobiliproteins and the third phycobiliprotein contains non-crosslinked subunits that exchange with the non-crosslinked subunits of the first and second phycobiliproteins; and (d) a fourth container which includes a third ligand conjugated to a third tandem dye, the third tandem dye including a fourth phycobiliprotein that contains crosslinked and non-crosslinked subunits, the fourth phycobiliprotein derived from the first bacterial or eukaryotic algae species and conjugated to a third partner dye; wherein, the first, second, third, and fourth phycobiliproteins are the same; or the fourth phycobiliprotein is different from the first, second, or third phycobiliproteins and the fourth phycobiliprotein contains non-crosslinked subunits that exchange with the non-crosslinked subunits of the first, second, or third phycobiliproteins. See, Table 10. Alternatively, the components of the composition may be present in one container.

TABLE 10

| Container | Container Components | Tandem Dye Components |
|---|---|---|
| 1 | ligand-1 conjugated to tandem dye-1 | phycobiliprotein-1 (species 1) conjugated to partner dye-1 |
| 2 | unconjugated phycobiliprotein-2 (species 1) | |
| 3 | ligand-2 conjugated to tandem dye-2 | phycobiliprotein-3 (species 1) conjugated to partner dye-2 |
| 4 | ligand-3 conjugated to tandem dye-3 | phycobiliprotein-4 (species 1) conjugated to partner dye-3 |
| 5 or more | optional components recited above | |

In still a further embodiment, a kit is provided and contains (a) a first container which includes a first ligand conjugated to a first tandem dye, the first tandem dye including a first phycobiliprotein that contains crosslinked and non-crosslinked subunits, the first phycobiliprotein derived from a first bacterial or eukaryotic algae species and conjugated to a first partner dye; (b) a second container which includes an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein; (c) a third container which includes a second ligand conjugated to a second tandem dye, the second tandem dye including a third phycobiliprotein that contains crosslinked and non-crosslinked subunits, the third phycobiliprotein derived from the first bacterial or eukaryotic algae species; conjugated to a second partner dye conjugated to the third phycobiliprotein; wherein, the first, second, and third phycobiliproteins are the same; or the third phycobiliprotein is different from the first and second phycobiliproteins and the third phycobiliprotein contains non-crosslinked subunits that exchange with the non-crosslinked subunits of the first and second phycobiliproteins; (d) a fourth container which includes a third ligand conjugated to a third tandem dye, the third tandem dye including a fourth phycobiliprotein that contains crosslinked and non-crosslinked subunits, the fourth phycobiliprotein derived from the first bacterial or eukaryotic algae species and conjugated to a third partner dye; wherein, the first, second, third, and fourth phycobiliproteins are the same; or the fourth phycobiliprotein is different from the first, second, or third phycobiliproteins and the fourth phycobiliprotein contains non-crosslinked subunits that exchange with the non-crosslinked subunits of the first, second, or third phycobiliproteins; and (e) a fifth container which includes a fourth ligand conjugated to a fourth tandem dye, the fourth tandem dye including a fifth phycobiliprotein that comprises crosslinked and non-crosslinked subunits, the fifth phycobiliprotein derived from the bacterial or eukaryotic algae species and conjugated to a fourth partner dye; wherein, the first, second, third, fourth, and fifth phycobiliproteins are the same; or the fifth phycobiliprotein is different from the first, second, third, or fourth phycobiliproteins and the fifth phycobiliprotein contains non-crosslinked subunits that exchange with the non-crosslinked subunits of the first, second, third, or fourth phycobiliproteins. See, Table 11. Alternatively, the components of the composition may be present in one container.

TABLE 11

| Container | Container Components | Tandem Dye Components |
|---|---|---|
| 1 | ligand-1 conjugated to tandem dye-1 | phycobiliprotein-1 (species 1) conjugated to partner dye-1 |
| 2 | unconjugated phycobiliprotein-2 (species 1) | |
| 3 | ligand-2 conjugated to tandem dye-2 | phycobiliprotein-3 (species 1) conjugated to partner dye-2 |
| 4 | ligand-3 conjugated to tandem dye-3 | phycobiliprotein-4 (species 1) conjugated to partner dye-3 |
| 5 | ligand-4 conjugated to tandem dye-4 | phycobiliprotein-5 (species 1) conjugated to partner dye-4 |
| 6 or more | optional components recited above | |

In yet another embodiment, a kit is provided and contains (a) a first container which includes a first ligand conjugated to a first tandem dye, the first tandem dye including a first phycobiliprotein that contains crosslinked and non-crosslinked subunits, the first phycobiliprotein derived from a first bacterial or eukaryotic algae species and conjugated to a first partner dye; (b) a second container which includes an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein; and (c) a third container which includes one or more additional ligands conjugated to a dye that is not a phycobiliprotein. See, Table 12. Alternatively, the components of the composition may be present in one container.

TABLE 12

| Container | Container Components | Tandem Dye Components |
|---|---|---|
| 1 | ligand-1 conjugated to tandem dye-1 | phycobiliprotein-1 (species 1) conjugated to partner dye-1 |
| 2 | unconjugated phycobiliprotein-2 (species 1) | |
| 3 | ligand-2 conjugated to non-phycobiliprotein dye-2 | |
| 4 or more | optional components recited above | |

In a further embodiment, a kit is provided and contains (a) a first container which includes a first ligand conjugated to a first tandem dye, the first tandem dye including a first phycobiliprotein that contains crosslinked and non-crosslinked subunits, the first phycobiliprotein derived from a first bacterial or eukaryotic algae species and conjugated to a first partner dye; (b) a second container which includes an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein; (c) a third container which includes a second ligand conjugated to a second tandem dye, the second tandem dye including a third phycobiliprotein that contains crosslinked and non-crosslinked subunits, the third phycobiliprotein derived from a second bacterial or eukaryotic algae species and conjugated to a second partner dye; and (d) a fourth container which includes an unconjugated fourth phycobiliprotein that contains subunits, the second phycobiliprotein derived from the second bacterial or eukaryotic algae species; wherein, the fourth phycobiliprotein and the third phycobiliprotein are the same; or the fourth phycobiliprotein and the third phycobiliprotein are different and the fourth phycobiliprotein contains non-crosslinked subunits that exchange with the non-crosslinked subunits of the third phycobiliprotein. See, Table 13. Alternatively, the components of the composition may be present in one container.

TABLE 13

| Container | Container Components | Tandem Dye Components |
|---|---|---|
| 1 | ligand-1 conjugated to tandem dye-1 | phycobiliprotein-1 (species 1) conjugated to partner dye-1 |
| 2 | unconjugated phycobiliprotein-2 (species 1) | |
| 3 | ligand-2 conjugated to tandem dye-2 | phycobiliprotein-3 (species 2) conjugated to partner dye-2 |
| 4 | unconjugated phycobiliprotein-4 (species 2) | |
| 5 or more | optional components recited above | |

In another embodiment, a kit is provided and contains (a) a first ligand conjugated to a first tandem dye, the first tandem dye a first phycobiliprotein that contains crosslinked and non-crosslinked subunits, the first phycobiliprotein derived from a first bacterial or eukaryotic algae species and conjugated to a first partner dye conjugated; (b) an unconjugated second phycobiliprotein that contains subunits, the second phycobiliprotein derived from the first bacterial or eukaryotic algae species; wherein, the second phycobiliprotein and the first phycobiliprotein are the same; or the second phycobiliprotein and the first phycobiliprotein are different and the second phycobiliprotein contains non-crosslinked subunits that exchange with the non-crosslinked subunits of the first phycobiliprotein; (c) a second ligand conjugated to a second tandem dye, the second tandem dye including a third phycobiliprotein that contains crosslinked and non-crosslinked subunits, the third phycobiliprotein derived from a second bacterial or eukaryotic algae species and conjugated to a second partner dye; (d) an unconjugated fourth phycobiliprotein that contains subunits, the second phycobiliprotein derived from the second bacterial or eukaryotic algae species; wherein, the fourth phycobiliprotein and the third phycobiliprotein are the same; or the fourth phycobiliprotein and the third phycobiliprotein are different and the fourth phycobiliprotein contains non-crosslinked subunits that exchange with the non-crosslinked subunits of the third phycobiliprotein; and (e) a third ligand conjugated to a fourth phycobiliprotein, the fourth phycobiliprotein derived from the first bacterial species, the first eukaryotic algae species, the second bacterial species, or the second eukaryotic algae species; wherein, the fourth phycobiliprotein is the same as the first phycobiliprotein, the second phycobiliprotein, or the third phycobiliprotein; or the fourth phycobiliprotein and is different from the first, second, or third phycobiliprotein and contains non-crosslinked subunits that exchange with the non-crosslinked subunits of the first, second, or third phycobiliprotein. See, Table 14. Alternatively, the components of the composition may be present in one container.

TABLE 14

| Container | Container Components | Tandem Dye Components |
|---|---|---|
| 1 | ligand-1 conjugated to tandem dye-1 | phycobiliprotein-1 (species 1) conjugated to partner dye-1 |
| 2 | unconjugated phycobiliprotein-2 (species 1) | |
| 3 | ligand-2 conjugated to tandem dye-2 | phycobiliprotein-3 (species 2) conjugated to partner dye-2 |
| 4 | unconjugated phycobiliprotein-4 (species 2) | |
| 5 | ligand-3 conjugated to phycobiliprotein (species 1 or 2) | |
| 6 or more | optional components recited above | |

The following examples illustrate various aspects of the invention. These examples do not limit the scope of this invention that is defined by the appended claims.

EXAMPLES

Example 1

This example was performed to determine the percentage of crosslinking in APC isolated from *Spirulina platensis*.

Various crosslinked and non-crosslinked APC samples were desalted on a Sephadex® G-50 column in PBS buffer (10 mM $K_3PO_4$+150 mM NaCl+2 mM EDTA pH 7.2). The desalted solutions were concentrated to about 15±2 mg/mL over a Micron® YM-30 membrane (Millipore Corporation, Part # UFC903024). These APC samples were next analyzed by HPLC using skill in the art and the following conditions/instruments.

| Column: | Superdex ® 200 HR size exclusion column (GE Health Care, Part #17-1088-01) |
|---|---|
| Eluent: | 10 mM $K_3PO_4$ + 150 mM NaCl + 2 mM EDTA + 1M $NaClO_4$ pH 7.2 |
| Flow rate: | 0.8 mL/min |

Figure 4:
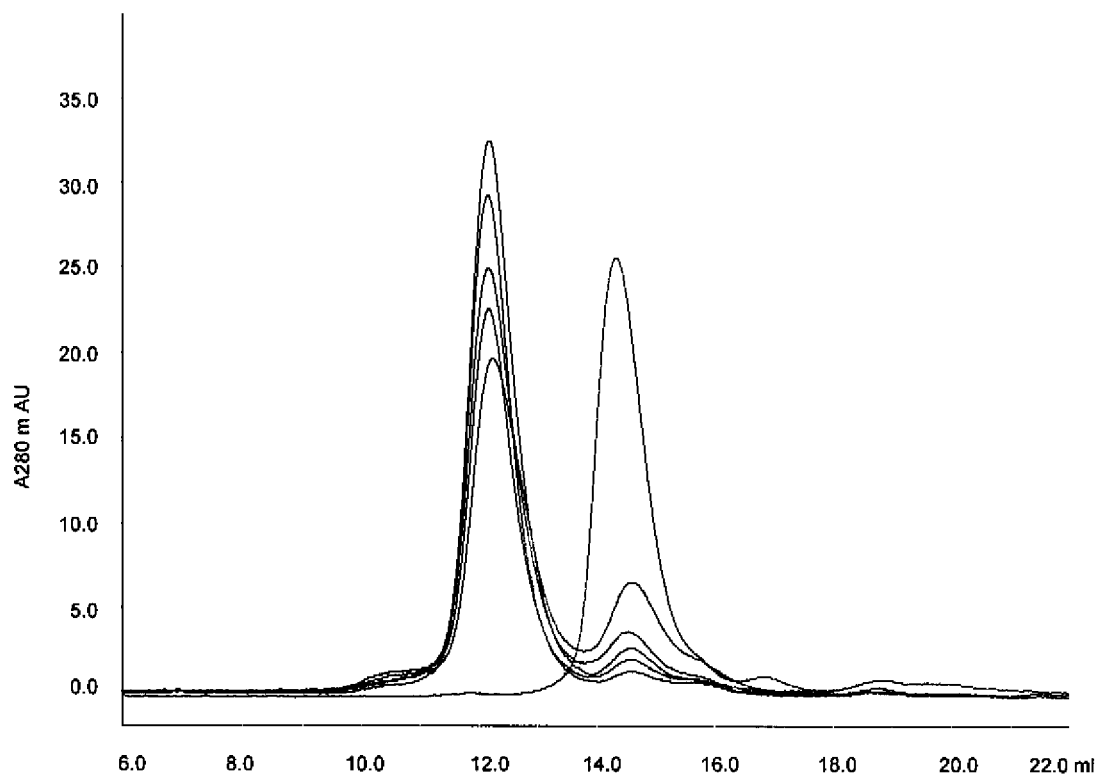
FIG. 4 provides a plot of wavelength ($A_{280}$) vs. size exclusion chromatography retention volume of APC samples isolated from *Spirulina platensis* having varying degrees of crosslinking and one (1) APC sample isolated from *Spirulina platensis* and having no crosslinking. The percentage of cross-linking in the APC was determined by calculating the area under the eluted peaks. The ratio of the integrated area of intact peak to the total area in a chromatogram gave the percentage of crosslinking for the sample. The tallest peak on the right side of the plot corresponds to the one (1) non-crosslinked APC sample. The remaining peaks of the plot correspond to the crosslinked APC samples. Specifically, the peaks on the left side of the plot correspond to the intact APC molecule and the small peaks on the right of the plot (under the non-crosslinked APC peak) correspond to the APC subunits.

Each of the concentrated APC samples was diluted to 0.5 mg/mL in buffer and incubated for 30 minutes at about 22±2° C. Each sample was then injected into the size exclusion column and wavelengths $A_{280}$, $A_{652}$ and $A_{616}$ were monitored during elution. The Plot of $A_{280}$ for representative samples and n-APC is shown in FIG. 4. Intact APC eluted at a retention volume of 12 mL and dissociated APC eluted at a retention volume of 14.5 mL. The percentage of cross-linking in the APC was determined by calculating the area under the eluted peaks. The ratio of the integrated area of intact peak to the total area in a chromatogram gave the percentage of cross-linking for the sample. FIG. 4 is the chromatogram of these crosslinked and non-crosslinked APC.

The tallest peak on the right side of the plot corresponds to the one (1) non-crosslinked APC sample. The remaining peaks of the plot correspond to the crosslinked APC samples. Specifically, the peaks on the left side of the plot correspond to the intact APC molecule and the small peaks on the right of the plot (under the non-crosslinked APC peak) correspond to the APC subunits. Based on these chromatograms, the percentage of crosslinking for the crosslinked APC samples was about 76 to about 96%.

Example 2

This example illustrates the advantage of the compositions and methods described herein which include 2-color ligand conjugated tandem dye compositions containing unconjugated phycobiliprotein.

Four (4) compositions were prepared and each contained two (2) monoclonal antibodies independently bound to a phycobiliprotein isolated from *Spirulina platensis* and a tandem dye. Specifically, each composition (10 µL) contained 0.5 µg of CD3 conjugated to allophycocyanin (CD3-APC) and 0.5 µg of CD19 conjugated to an allophycocyanin-AlexaFluor®750 tandem dye (CD19-APC-AlexaFluor®750).

Composition 1, i.e., the control composition, was freshly prepared and contained no additional components. Composition 2 contained no additional components but had been retained at 2 to 8° C. for 21 days. Compositions 3 and 4 also contained 0.5 µg of unconjugated APC isolated from *Spirulina platensis*, composition 3 being a fresh mix of all the components while composition 4 was retained for 21 days at 2 to 8° C. prior to addition to a biological specimen and analysis.

These compositions were then independently combined with a biological specimen containing whole blood (0.1 mL), incubated for 10-12 minutes, processed using the standard VersaLyse® method, and analyzed using a flow cytometer. One of skill in the art would readily be able to perform the VersaLyse® method as known in the art to include combining the treated biological specimen with the Versalyse® reagent/0.2% Formaldehyde (1 mL) for 10 minutes, spinning down the treated specimen, aspirating the supernatant, resuspending the pellet in PBS (3 mL), spinning down the PBS solution, and resuspending the pellet in PBS/0.1% Formaldehyde (0.5 ml) for analysis. See, FIGS. 1A-1D.

These results clearly show the usefulness of the composition of invention (FIG. 1D) as compared with the prior art (FIG. 1B) for flow cytometric analyses.

Example 3

This example illustrates the advantage of the compositions and methods described herein which involve adding unconjugated phycobiliprotein to a 2-color ligand conjugated tandem dye composition.

Nine (9) compositions were prepared and each contained two (2) monoclonal antibodies independently bound to a phycobiliprotein and a tandem dye. Specifically, each composition (10 µL) contained CD3 conjugated to allophycocyanin isolated from *Spirulina platensis* (0.5 µg; CD3-APC) and 0.5 µg of CD19 conjugated to an allophycocyanin (isolated from *Spirulina platensis*)-AlexaFluor®750 tandem dye (CD19-APC-AlexaFluor®750). Composition 1, i.e., the "prior art fresh mixture", was freshly prepared and contained no additional components. Composition 2, i.e., the "prior art stored mixture", contained no additional components but had been retained at 2 to 8° C. for 21 days. Compositions 3-9 also contained varying amounts of unconjugated APC isolated from *Spirulina platensis* and were retained for 21 days at 2 to 8° C. prior to addition to a biological specimen and analysis. See, Table 15.

TABLE 15

| Composition | Amount Unconjugated APC (µg)/10 µL of composition | Ratio of Unconjugated APC to CD3 or CD19 |
|---|---|---|
| 1 | None | N/A |
| 2 | None | N/A |
| 3 | 0.0625 | 0.125:1 |
| 4 | 0.125 | 0.25:1 |
| 5 | 0.25 | 0.5:1 |
| 6 | 0.5 | 1:1 |
| 7 | 2.0 | 4:1 |
| 8 | 5.0 | 10:1 |
| 9 | 10 | 20:1 |

These compositions were then used as in Example 2 above for flow cytometric analysis of a blood specimen. See, FIGS. 2A-2I.

Figure 1A:
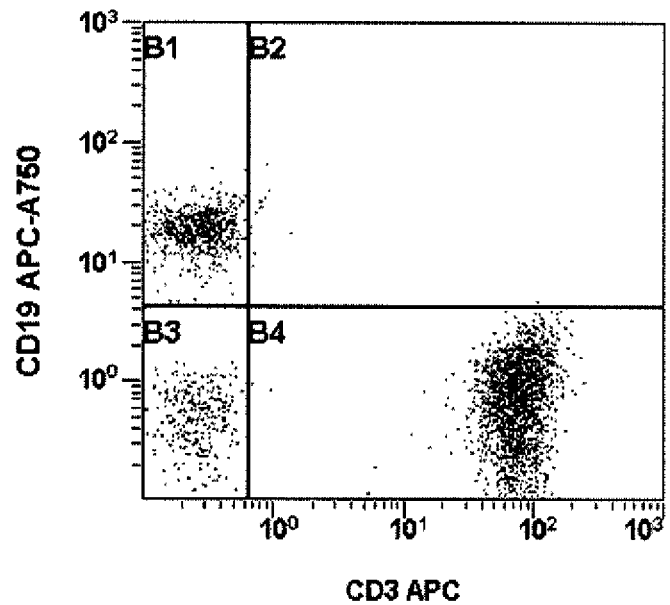
Figure 1B:
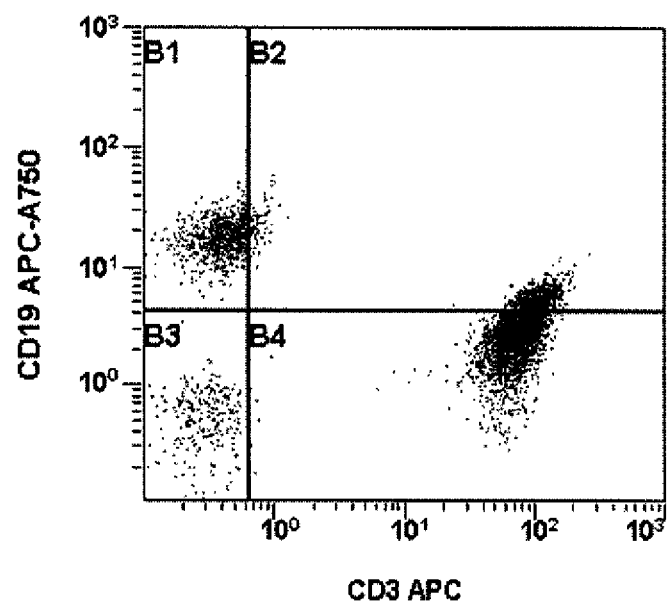
FIG. 1B provides a dual parameter histogram of a specimen prepared using, and demonstrating the effects of, a composition available in the prior art containing CD3-APC (0.5 µg) and CD19-APC-AlexaFluor®750 tandem dye (0.5 µg), i.e., the "prior art stored mixture", preformulated at 2 to 8° C. for and retained for 21 days. The APC in both conjugates is from the same bacterial species, i.e., *Spirulina platensis*. No free (unconjugated) APC is present.
Figure 1C:
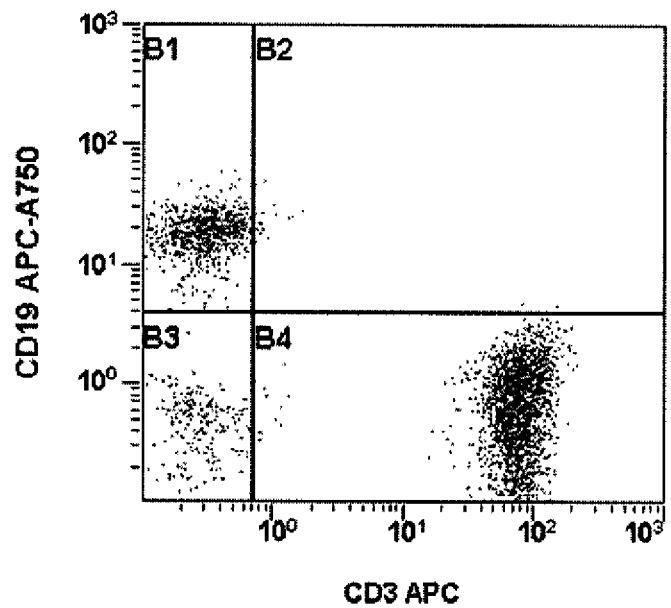
FIG. 1C provides a dual parameter histogram of a specimen prepared using, and demonstrating the effects of, a two-color reagent composition described herein containing CD3-APC (0.5 µg), CD19-APC-AlexaFluor®750 tandem dye (0.5 µg), and unconjugated APC (0.5 µg) freshly formulated from components individually stored at 2 to 8° C. for 21 days.
Figure 1D:
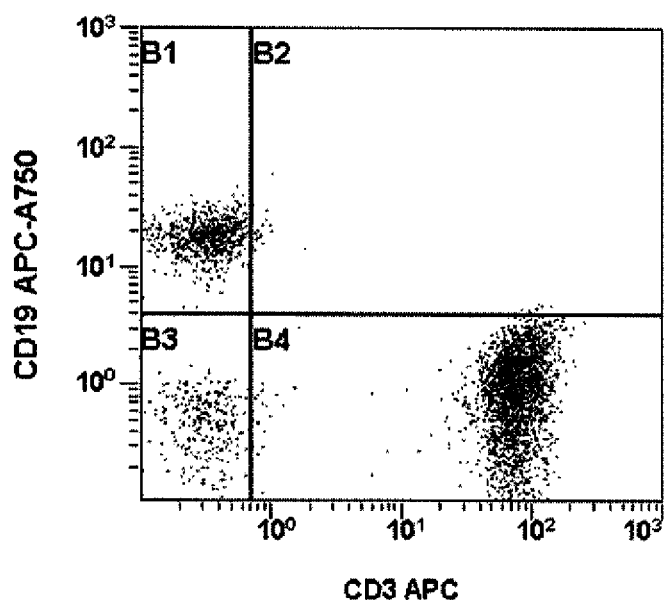
FIG. 1D provides a dual parameter histogram of the same specimen prepared using, and demonstrating the effects of, a two-color reagent composition described herein containing CD3-APC (0.5 µg), CD19-APC-AlexaFluor®750 tandem dye (0.5 µg), and unconjugated APC (0.5 µg), preformulated at 2 to 8° C. for 21 days.
Figure 2A:
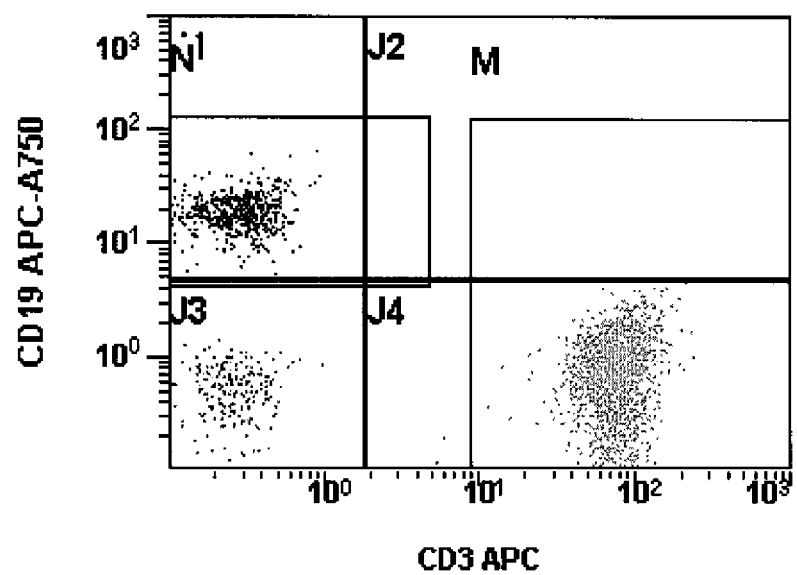
FIG. 2A provides a dual parameter fluorescence histogram of a freshly prepared control specimen using a two-color reagent composition of the prior art containing CD3-APC (0.5 µg) and CD19-APC-AlexaFluor®750 tandem dye (0.5 µg), i.e., the "prior art fresh mixture".
Figure 2B:
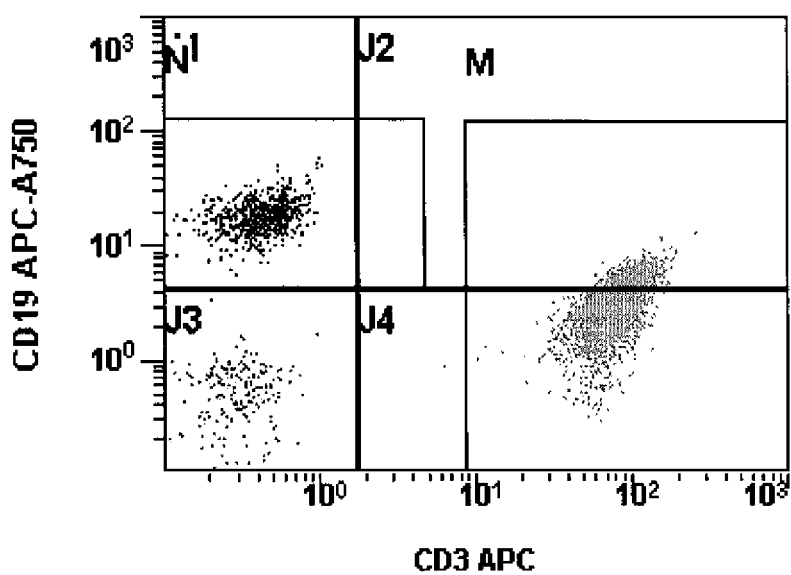
FIG. 2B provides a dual parameter fluorescence histogram of a specimen using a two-color reagent composition of the prior art containing CD3-APC (0.5 µg) and CD19-APC-AlexaFluor®750 tandem dye (0.5 µg) and retained at 2 to 8° C. for 21 days, i.e., the "prior art stored mixture".
Figure 2C:
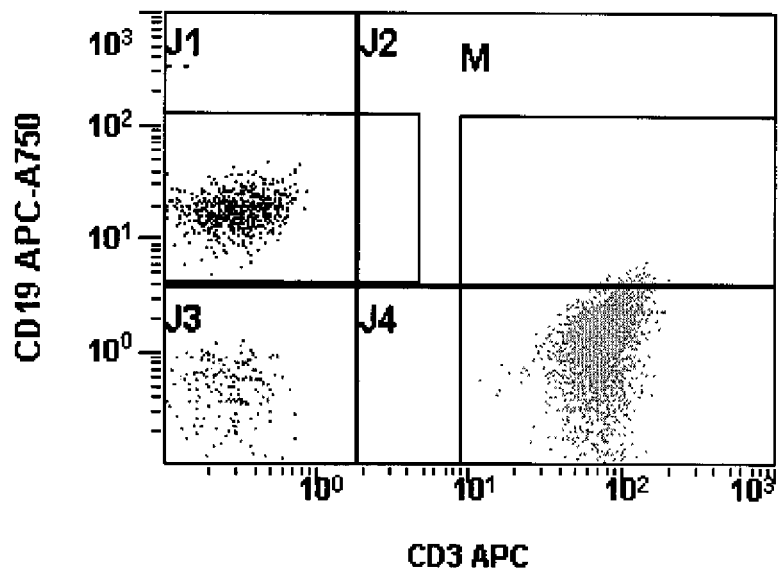
FIG. 2C provides a dual parameter fluorescence histogram of a specimen using a two-color reagent composition described herein containing CD3-APC (0.5 µg), CD19-APC-AlexaFluor®750 tandem dye (0.5 µg), and 0.0625 µg of native, unconjugated APC and retained at 2 to 8° C. for 21 days.
Figure 2D:
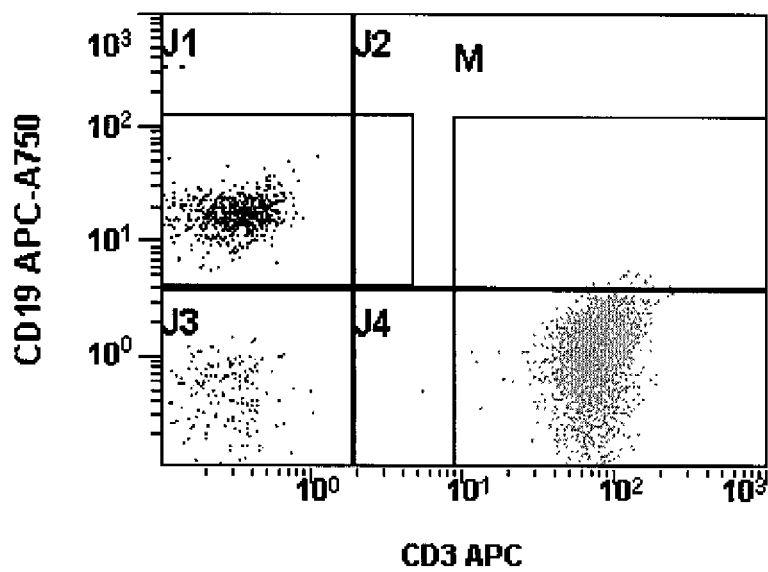
FIG. 2D provides a dual parameter fluorescence histogram of a specimen using a two-color reagent composition described herein containing CD3-APC (0.5 µg), CD19-APC-AlexaFluor®750 tandem dye (0.5 µg), and 0.125 µg of native, unconjugated APC and retained at 2 to 8° C. for 21 days.
Figure 2E:
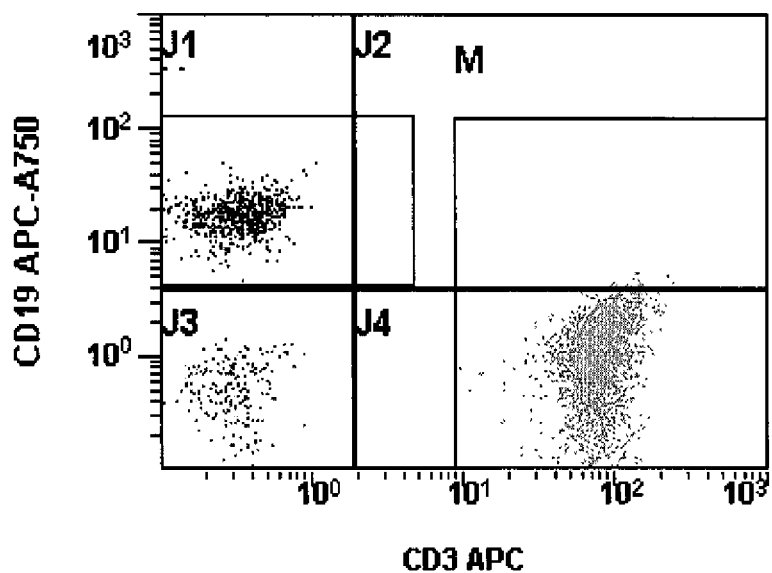
FIG. 2E provides a dual parameter fluorescence histogram of a specimen using a two-color reagent composition described herein containing CD3-APC (0.5 µg), CD19-APC-AlexaFluor®750 tandem dye (0.5 µg), and 0.25 µg of native, unconjugated APC and retained at 2 to 8° C. for 21 days.
Figure 2F:
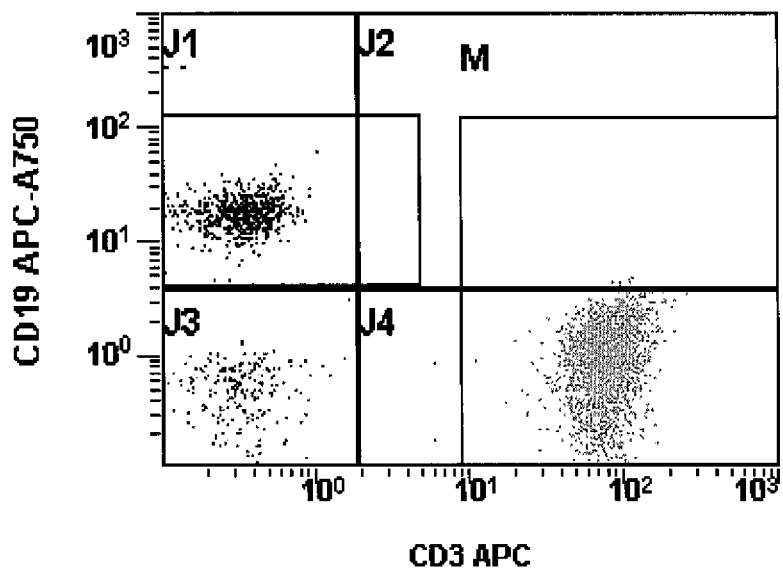
FIG. 2F provides a dual parameter fluorescence histogram of a specimen using a two-color reagent composition described herein containing CD3-APC (0.5 µg), CD19-APC-AlexaFluor®750 tandem dye (0.5 µg), and 0.5 µg of native, unconjugated APC and retained at 2 to 8° C. for 21 days.
Figure 2G:
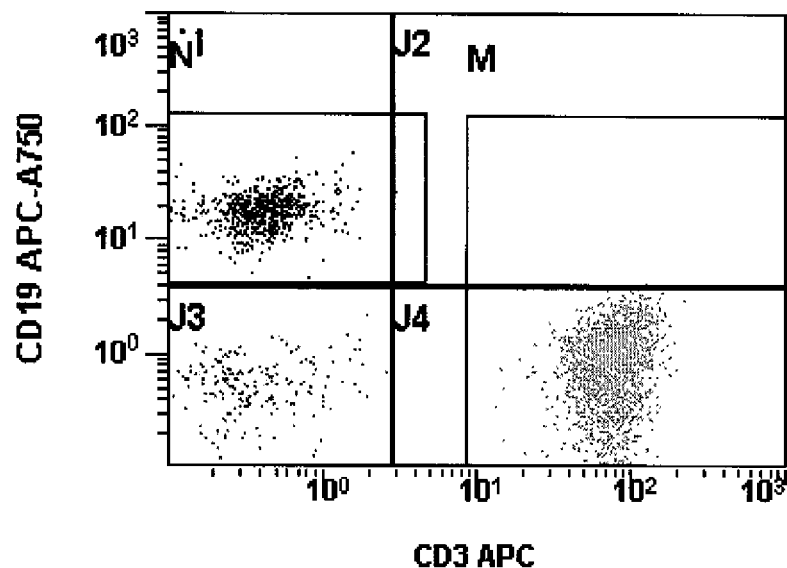
FIG. 2G provides a dual parameter fluorescence histogram of a specimen using a two-color reagent composition described herein containing CD3-APC (0.5 µg), CD19-APC-AlexaFluor® 750 tandem dye (0.5 µg), and 2.0 µg of native, unconjugated APC and retained at 2 to 8° C. for 21 days.
Figure 2H:
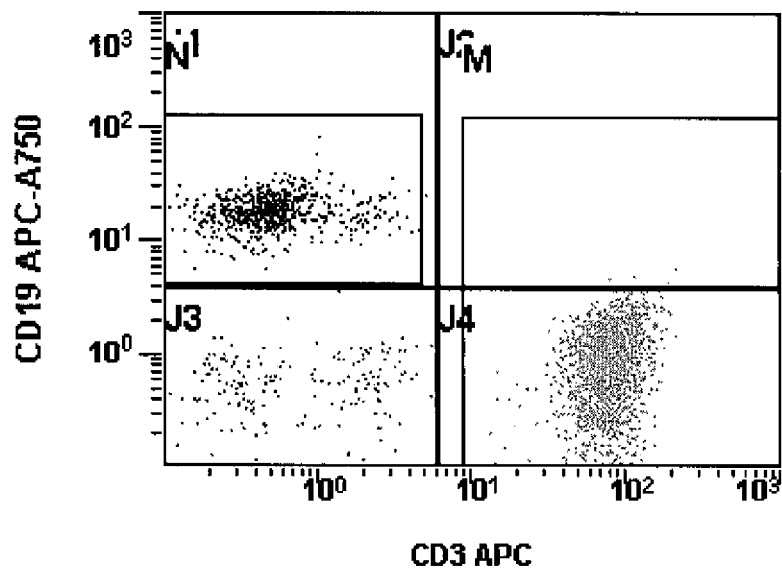
FIG. 2H provides a dual parameter fluorescence histogram of a specimen using a two-color reagent composition described herein containing CD3-APC (0.5 µg), CD19-APC-AlexaFluor®750 tandem dye (0.5 µg), and 5.0 µg of native, unconjugated APC and retained at 2 to 8° C. for 21 days.
Figure 2I:
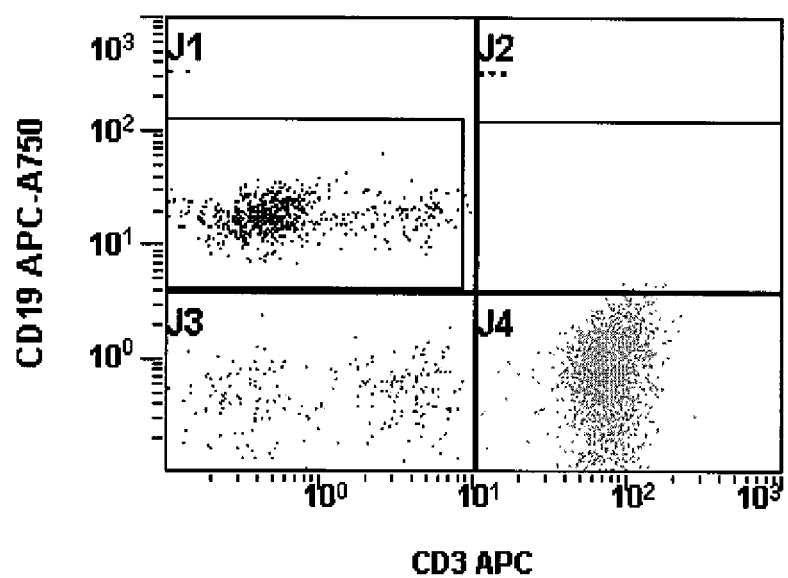
FIG. 2I provides a dual parameter fluorescence histogram of a specimen using a two-color reagent composition described herein containing CD3-APC (0.5 µg), CD19-APC-AlexaFluor®750 tandem dye (0.5 µg), and 10 µg of native, unconjugated APC and retained at 2 to 8° C. for 21 days. Comparison of FIGS. 2A and 2B with 2C through 2I demonstrates the enhanced stability of the compositions described herein vs. those of the prior art.
Figure 3A:
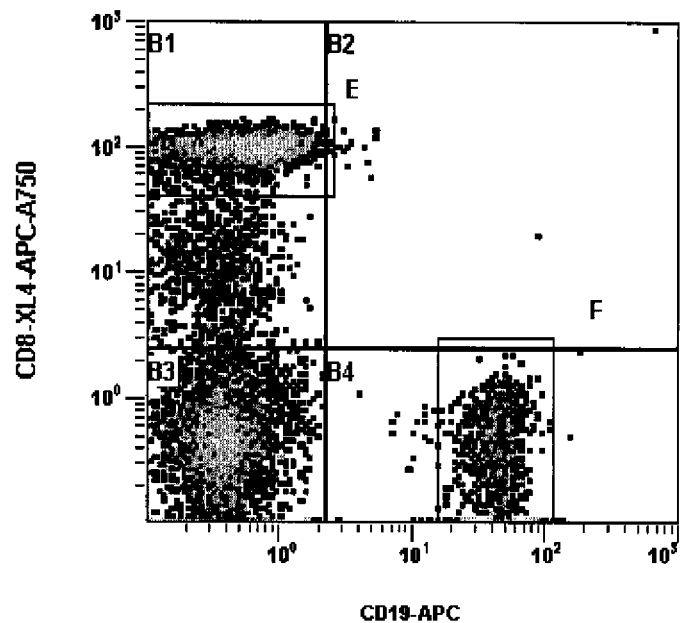
Figure 3B:
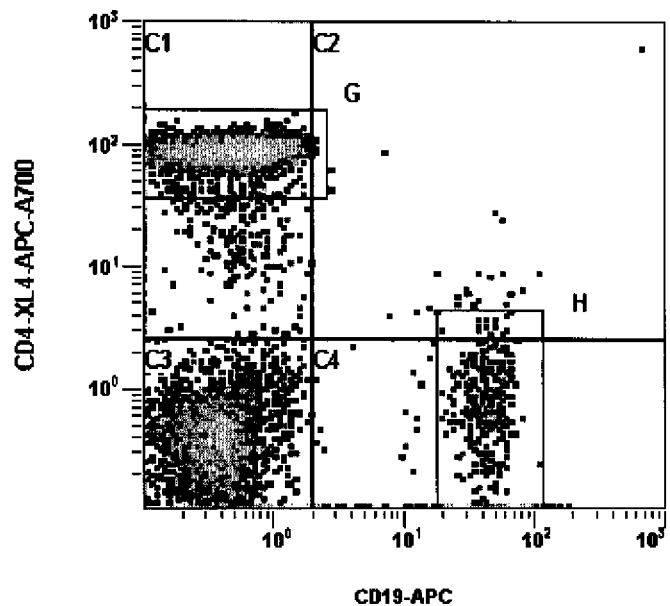
Figure 3C:
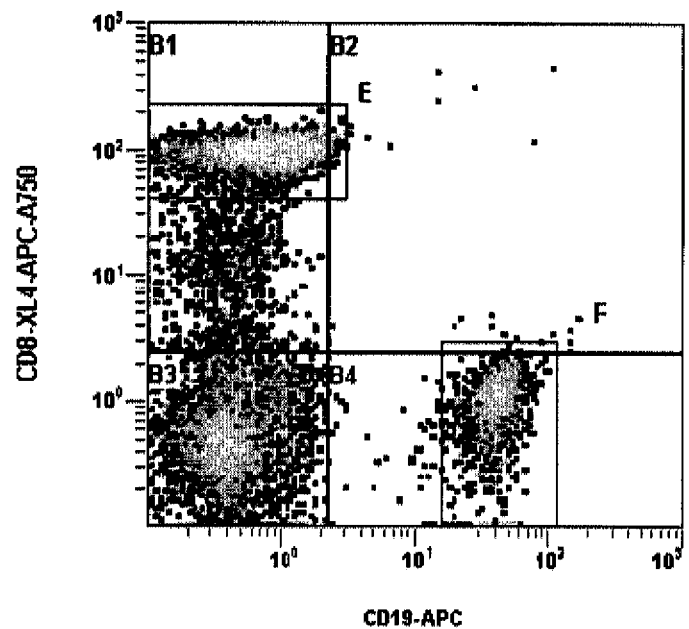
Figure 3D:
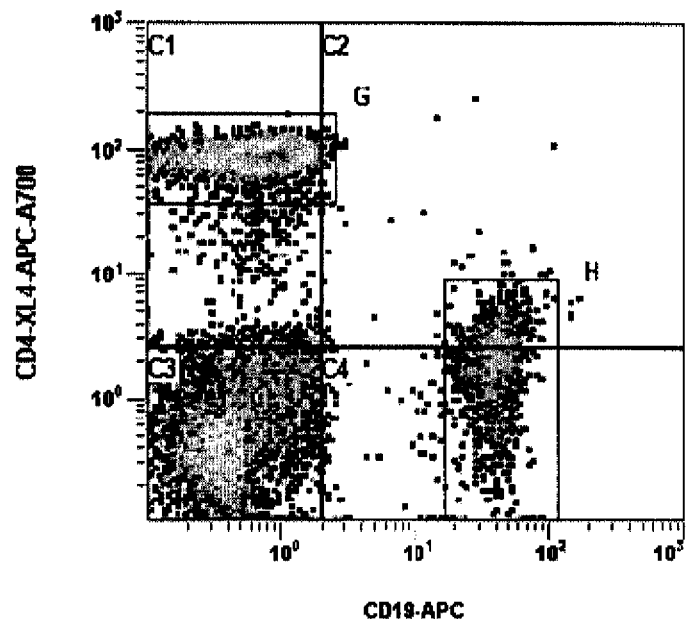
Figure 3E:
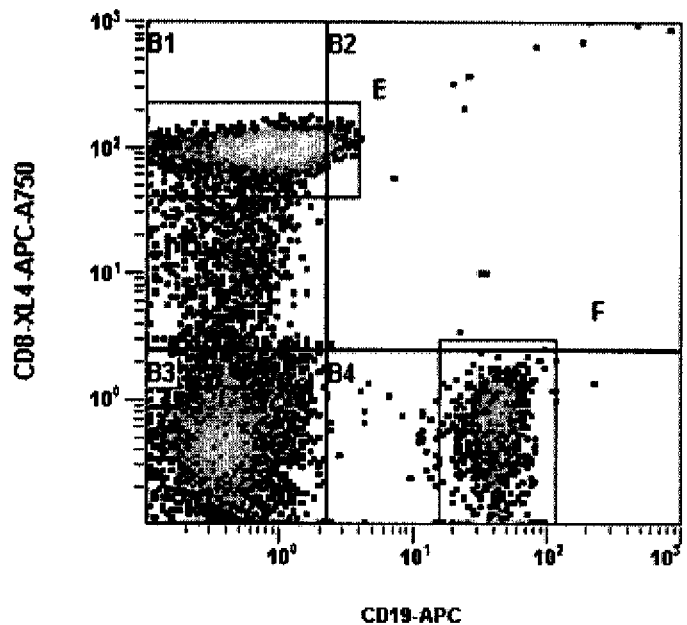
Figure 3F:
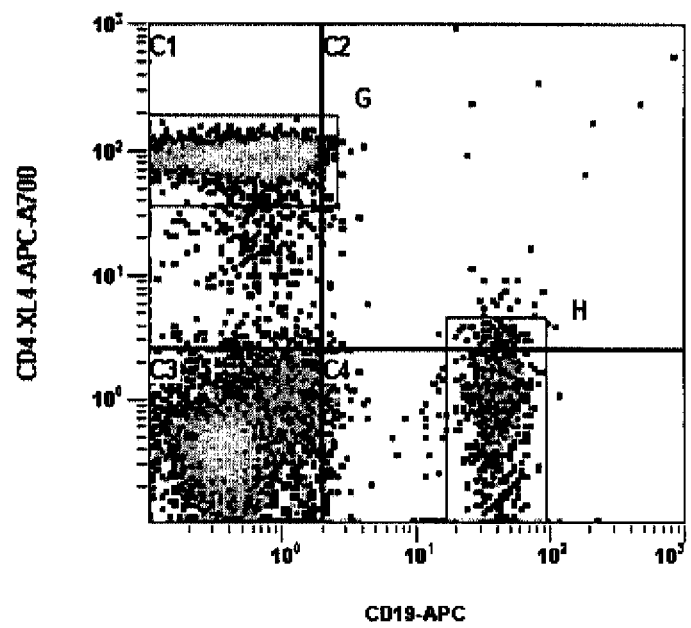
Figure 3G:
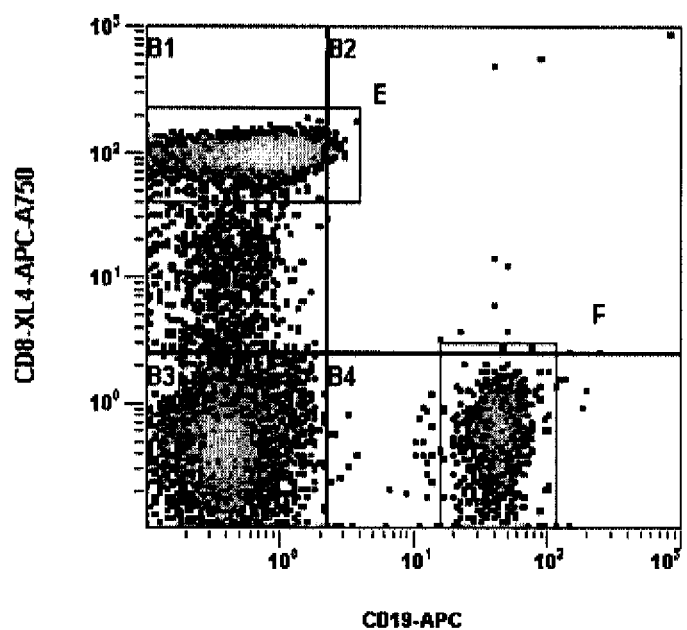
Figure 3H:
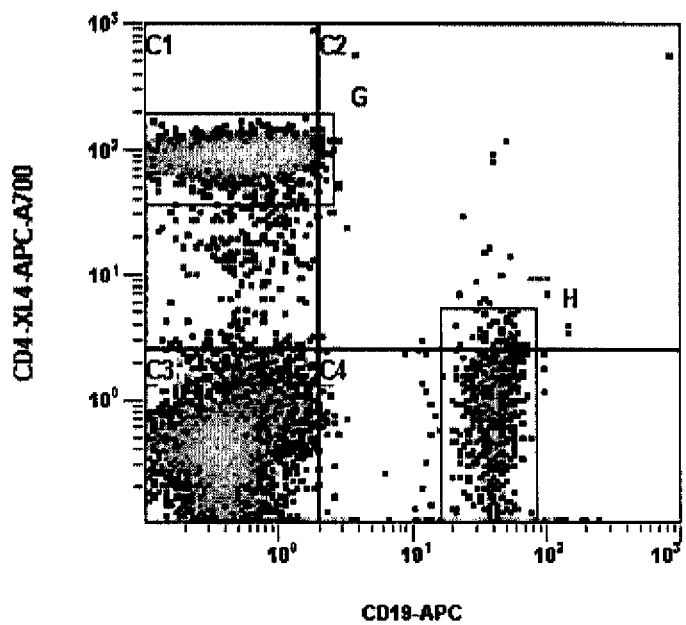
Figure 3I:
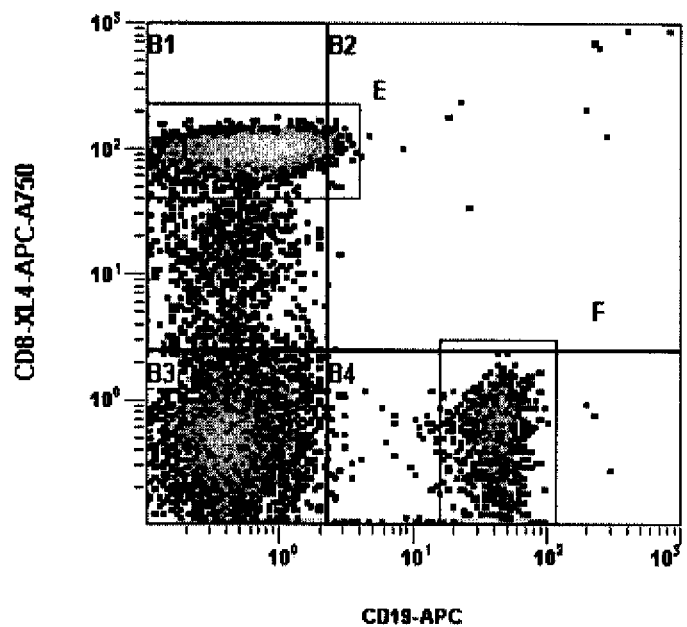
Figure 3J:
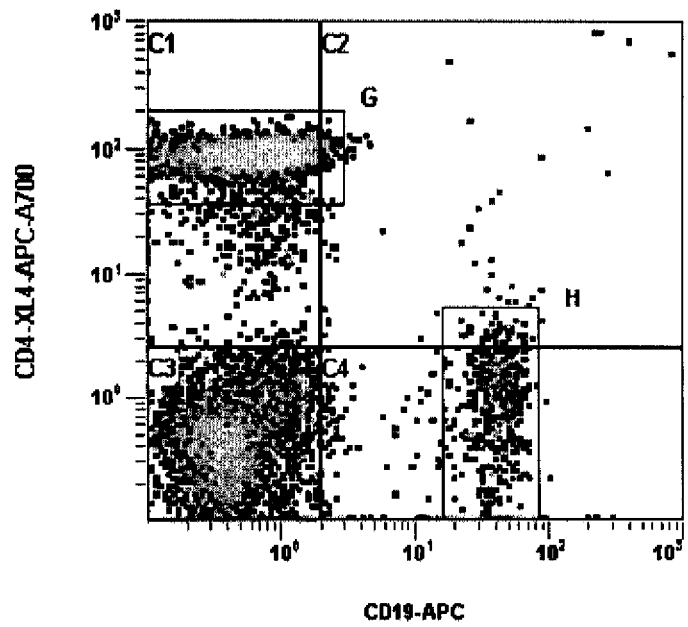

These results illustrate the usefulness of adding native unconjugated APC (over a broad range) to a two color ligand conjugated APC tandem dye and ligand conjugated APC reagent composition in minimizing the effect of subunit exchange. Higher concentrations (especially 500 µg/mL and above) lead to increasing non-specific labeling of cells. Unconjugated APC in amounts from 0.0625 µg (FIG. 2C) to 2 µg (FIG. 2G), however, showed no such increase in non-specific labeling of cells and also provided the desired stability to the compositions of the prior art (FIG. 2B). The results also illustrate that addition of free, unconjugated phycobiliprotein ranging from 0.0625 µg to 10.0 µg limits the degradation of the preformulated product over time.

Example 4

This example illustrates the advantage of the compositions and methods described herein which involve adding unconjugated phycobiliprotein to a 3-color ligand conjugated phycobiliprotein and ligand conjugated tandem dyes composition. Five (5) compositions were prepared and contained three (3) monoclonal antibodies independently bound to a phycobiliprotein isolated from *Spirulina platensis* and the two tandem dyes. Specifically, each composition (10 µL) contained 0.5 µg of CD19 conjugated to allophycocyanin isolated from *Spirulina platensis* (CD19-APC), 0.5 µg of CD4 conjugated to an allophycocyanin (isolated from *Spirulina platensis*)-AlexaFluor®700 tandem dye (CD19-APC-A700), and 0.5 µg of CD8 conjugated to an allophycocyanin (isolated from *Spirulina platensis*)-AlexaFluor®750 tandem dye (CD8-APC-A750). Composition 1, i.e., the control composition, was freshly prepared and contained no additional components. Composition 2 contained no additional components but had been retained at 2 to 8° C. for 120 days. Compositions 3-5 contained, in addition, varying amounts of unconjugated APC isolated from *Spirulina platensis* and retained for 120 days at 2 to 8° C. prior to analysis. See, Table 16.

TABLE 16

| Composition | Amount Unconjugated APC (µg)/10 µL of composition | Ratio of Unconjugated APC to CD3 CD8 or CD19 |
|---|---|---|
| 1 | none | N/A |
| 2 | none | N/A |
| 3 | 0.5 | 1:1 |
| 4 | 1.0 | 2:1 |
| 5 | 2.0 | 4:1 |

These compositions were then independently used to analyze a blood specimen as in Example 2. See FIGS. 3A-3J. These figures demonstrate the stability of the ligand-dye compositions during storage using different amounts of free phycobiliprotein. These results thereby illustrate that free, unconjugated phycobiliprotein limits the degradation of the preformulated composition over time in a more complex mixture of a three-color reagent.

All published documents, patents and patent applications, as well as the disclosures of the priority documents recited above, are incorporated herein by reference. Numerous conventional modifications and variations of the methods and compositions described herein are included in the above-identified specification and are expected to be obvious to one of skill in the art. Such modifications and alterations to the compositions and processes of the various embodiments of the invention are believed to be encompassed in the scope of the claims appended hereto.

What is claimed is:

1. A composition comprising:
   (a) a first ligand conjugated to a first tandem dye, said first tandem dye comprising:
      (i) a first phycobiliprotein component comprising two or more linked subunits, said two or more linked subunits including covalently bonded crosslinked and non-crosslinked subunits, wherein said first phycobiliprotein component is derived from a first bacterial species or first eukaryotic algae species; and
      (ii) a first partner dye conjugated to said first phycobiliprotein, wherein said first partner dye is a non-phycobiliprotein dye; and
   (b) a second phycobiliprotein component comprising two or more linked subunits, said two or more linked subunits including non-crosslinked subunits, wherein said second phycobiliprotein component is derived from said first bacterial species or said first eukaryotic algae species, and wherein said second phycobiliprotein component is not conjugated to a non-phycobiliprotein dye;
   wherein said second phycobiliprotein component and said first phycobiliprotein component are the same; or said second phycobiliprotein component and said first phycobiliprotein component are different, and
   wherein a subunit exchange occurs between said non-crosslinked subunits of said second phycobiliprotein component with said non-crosslinked subunits of said first phycobiliprotein component.

2. The composition according to claim 1, wherein when said first phycobiliprotein component and said second phycobiliprotein component are different, said second phycobiliprotein component contains no crosslinked subunits between said two or more linked subunits.

3. The composition according to claim 1, wherein said second phycobiliprotein component further comprises covalently bonded crosslinked subunits between said two or more linked subunits.

4. The composition according to claim 1, wherein when said second phycobiliprotein component includes covalently bonded crosslinked subunits between said two or more linked subunits, said second phycobiliprotein component is a native protein or a modified protein, and when said second phycobiliprotein component includes no crosslinked subunits between said two or more linked subunits said second phycobiliprotein component is a modified protein.

5. The composition according to claim 1, wherein when the first and second phycobiliprotein components are different, the amount of covalently bonded crosslinked subunits between said two or more linked subunits in said first phycobiliprotein component is greater than the amount of covalently bonded crosslinked subunits between said two or more linked subunits in said second phycobiliprotein component.

6. The composition according to claim 1, wherein said second phycobiliprotein component is bleached.

7. The composition according to claim 1, wherein the ratio of said second phycobiliprotein component to said first phycobiliprotein component is about 0.25:1 to about 10:1.

8. The composition according to claim 1, wherein said first phycobiliprotein component and said second phycobiliprotein component are allophycocyanin, phycoerythrin, phycocyanin, or phycoerythrocyanin.

9. The composition according to claim 8, wherein said first phycobiliprotein component and said second phycobiliprotein component are R-phycoerythrin, B-phycoerythrin, Y-phycoerythrin, phycoerythrin 566, phycoerythrocyanin, R-phycocyanin, or allophycocyanin.

10. The composition according to claim 8, wherein said first phycobiliprotein component and said second phycobiliprotein component are allophycocyanins.

11. The composition according to claim 1, wherein said first bacterial species is a cyanobacterium.

12. The composition according to claim 1, further comprising a second, third or fourth ligand or a combination thereof selected from the group consisting of:
 (c) a second ligand conjugated to a second tandem dye, said second tandem dye comprising:
  (i) a third phycobiliprotein component comprising two or more linked subunits, said two or more linked subunits including covalently bonded crosslinked and non-crosslinked subunits, wherein said third phycobiliprotein component is derived from said first bacterial species or said first eukaryotic algae species; and
  (ii) a second partner dye conjugated to said third phycobiliprotein, wherein said second partner dye is a non-phycobiliprotein dye; and
  wherein said first phycobiliprotein component, said second phycobiliprotein component, and said third phycobiliprotein component are the same; or said third phycobiliprotein component is different from said first phycobiliprotein component and said second phycobiliprotein components, and
  wherein a subunit exchange occurs between said non-crosslinked subunits of said third phycobiliprotein component with said non-crosslinked subunits of said first phycobiliprotein component or said second phycobiliprotein components;
 (d) a third ligand conjugated to a third tandem dye, said third tandem dye comprising:
  (i) a fourth phycobiliprotein component comprising two or more linked subunits, said two or more linked subunits including covalently bonded crosslinked and non-crosslinked subunits, wherein said fourth phycobiliprotein component is derived from said first bacterial species or said first eukaryotic algae species; and
  (ii) a third partner dye conjugated to said fourth phycobiliprotein, wherein said fourth partner dye is a non-phycobiliprotein dye; and
  wherein said first phycobiliprotein component, said second phycobiliprotein component, said third phycobiliprotein component, and said fourth phycobiliprotein component are the same; or said fourth phycobiliprotein component is different from said first phycobiliprotein component, said second phycobiliprotein component, or said third phycobiliprotein component, and
  wherein a subunit exchange occurs between said non-crosslinked subunits of said fourth phycobiliprotein component with said non-crosslinked subunits of said first phycobiliprotein component, said second phycobiliprotein component, or said third phycobiliprotein component; or
 (e) a fourth ligand conjugated to a fourth tandem dye, said fourth tandem dye comprising:
  (i) a fifth phycobiliprotein component comprising two or more linked subunits, said two or more linked subunits including covalently bonded crosslinked and non-crosslinked subunits, wherein said fifth phycobiliprotein component is derived from said first bacterial species or said first eukaryotic algae species; and
  (ii) a fourth partner dye conjugated to said fifth phycobiliprotein, wherein said fifth partner dye is a non-phycobiliprotein dye; and
  wherein: said first phycobiliprotein component, said second phycobiliprotein component, said third phycobiliprotein component, said fourth phycobiliprotein component, and said fifth phycobiliprotein component are the same; or said fifth phycobiliprotein component is different from said first phycobiliprotein component, said second phycobiliprotein component, said third phycobiliprotein component, or said fourth phycobiliprotein component, and
  wherein a subunit exchange occurs between said non-crosslinked subunits of said fifth phycobiliprotein component with said non-crosslinked subunits of said first phycobiliprotein component, said second phycobiliprotein component, said third phycobiliprotein component, or said fourth phycobiliprotein component.

13. The composition according to claim 1, further comprising one or more additional ligands conjugated to a dye that is not a phycobiliprotein.

14. The composition according to claim 1, further comprising:
 (c) a second ligand conjugated to a third phycobiliprotein component comprising two or more linked subunits, wherein said third phycobiliprotein component is derived from said first bacterial species or said first eukaryotic algae species;
  wherein said third phycobiliprotein component is the same as said first phycobiliprotein component or said second phycobiliprotein component; or said third phycobiliprotein component is different from said first phycobiliprotein component or said second phycobiliprotein component, and said third phycobiliprotein component comprising said two or more linked subunits comprises non-crosslinked subunits that exchange with said non-crosslinked subunits of first or second phycobiliproteins; or wherein said third phycobiliprotein component is different from said first phycobiliprotein component or said second phycobiliprotein component and wherein said third phycobiliprotein component comprising said two or more linked subunits does not comprise non-crosslinked subunits that exchange with non-crosslinked subunits of said first phycobiliprotein component or said second phycobiliprotein component.

15. The composition according to claim 1, further comprising:
   (c) a second ligand conjugated to a second tandem dye, said second tandem dye comprising:
      (i) a third phycobiliprotein component comprising two or more linked subunits, said two or more linked subunits including covalently bonded crosslinked and non-crosslinked subunits, wherein said third phycobiliprotein component is derived from a second bacterial species or a second eukaryotic algae species; and
      (ii) a second partner dye conjugated to said third phycobiliprotein, wherein said second partner dye is a non-phycobiliprotein dye;
   (d) a fourth phycobiliprotein component comprising two or more linked subunits, said two or more linked subunits including non-crosslinked subunits, wherein said fourth phycobiliprotein component is derived from said second bacterial species or said second eukaryotic algae species, and wherein said second phycobiliprotein component is not conjugated to a non-phycobiliprotein dye;
      wherein said fourth phycobiliprotein component and said third phycobiliprotein component are the same; or said fourth phycobiliprotein component and said third phycobiliprotein component are different, and
      wherein a subunit exchange occurs between said non-crosslinked subunits of said fourth phycobiliprotein component with said non-crosslinked subunits of said third phycobiliprotein component; and
   (e) optionally a third ligand conjugated to a fourth phycobiliprotein component comprising two or more linked subunits, wherein said fourth phycobiliprotein component is derived from said first bacterial species, said first eukaryotic algae species, said second bacterial species, or said second eukaryotic algae species;
      wherein said fourth phycobiliprotein component is the same as said first phycobiliprotein component, said second phycobiliprotein component, or said third phycobiliprotein component; or said fourth phycobiliprotein component is different from said first phycobiliprotein component, said second phycobiliprotein component, or said third phycobiliprotein component, and
      wherein a subunit exchange occurs between said non-crosslinked subunits of said fourth phycobiliprotein component with said non-crosslinked subunits of said first phycobiliprotein component, said second phycobiliprotein component, or said third phycobiliprotein component.

16. A method for analyzing cellular and non-cellular populations in a specimen, the method comprising:
   (a) combining said specimen and a composition of claim 1, wherein at least one of said cellular and non-cellular populations comprise receptors for said first ligand; and
   (b) identifying said populations in said specimen by analyzing fluorescence.

17. The method according to claim 16, further comprising identifying at least one additional parameter independently selected from the group consisting of one or more channels of fluorescence, one or more optical parameters, one or more electrical parameters, time, scatter, and combinations thereof.

18. A kit comprising the components of a composition of claim 1.

19. The composition according to claim 11, wherein said cyanobacterium is *Spirulina platensis, Anabaena variabilis, Gloeobacter violaceus, Tolypothrix tenuis*, or *Lyngbya lagerheimii*.

* * * * *

UNITED STATES PATENT AND TRADEMARK OFFICE
CERTIFICATE OF CORRECTION

| | |
|---|---|
| PATENT NO. | : 8,663,935 B2 |
| APPLICATION NO. | : 12/635063 |
| DATED | : March 4, 2014 |
| INVENTOR(S) | : Wolfers et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 532 days.

Signed and Sealed this
Twenty-first Day of July, 2015

Michelle K. Lee
*Director of the United States Patent and Trademark Office*